United States Patent
Brook et al.

(10) Patent No.: US 7,268,156 B2
(45) Date of Patent: Sep. 11, 2007

(54) CARVEDILOL PHOSPHATE SALTS AND/OR SOLVATES THEREOF, CORRESPONDING COMPOSITIONS AND/OR METHODS OF TREATMENT

(75) Inventors: Christopher S. Brook, King of Prussia, PA (US); Wei Chen, Woodbury, MN (US); Paul G. Spoors, King of Prussia, PA (US)

(73) Assignee: SB Pharmco Puerto Rico Inc., Hato Rey, PR (US)

( * ) Notice: Subject to any disclaimer, the term of this patent is extended or adjusted under 35 U.S.C. 154(b) by 0 days.

(21) Appl. No.: 10/518,654

(22) PCT Filed: Jun. 27, 2003

(86) PCT No.: PCT/US03/20408

§ 371 (c)(1),
(2), (4) Date: Dec. 16, 2004

(87) PCT Pub. No.: WO2004/002419

PCT Pub. Date: Jan. 8, 2004

(65) Prior Publication Data

US 2005/0240027 A1    Oct. 27, 2005

Related U.S. Application Data

(60) Provisional application No. 60/392,175, filed on Jun. 27, 2002.

(51) Int. Cl.
*C07D 209/88* (2006.01)
*A61K 31/403* (2006.01)

(52) U.S. Cl. ........................ 514/411; 548/444
(58) Field of Classification Search .................... None
See application file for complete search history.

(56) References Cited

U.S. PATENT DOCUMENTS

| | | | |
|---|---|---|---|
| 4,053,067 A * | 10/1977 | Katz et al. .................... 376/268 |
| 4,503,067 A * | 3/1985 | Wiedemann et al. ....... 514/411 |
| 4,985,464 A | 1/1991 | Happle et al. |
| 5,071,868 A | 12/1991 | Leinert |
| 5,308,862 A | 5/1994 | Ohlstein |
| 5,393,772 A | 2/1995 | Yue et al. |
| 5,405,863 A | 4/1995 | Barone et al. |
| 5,453,436 A | 9/1995 | Ohlstein |
| 5,643,939 A | 7/1997 | Ohlstein |
| 5,760,069 A | 6/1998 | Lukas-Laskey et al. |
| 5,902,821 A | 5/1999 | Lukas-Laskey et al. |
| 6,096,777 A | 8/2000 | Feuerstein et al. |
| 6,214,854 B1 | 4/2001 | Wang et al. |
| 6,358,990 B1 | 3/2002 | Howlett et al. |
| 6,403,579 B1 | 6/2002 | Heller |
| 6,515,010 B1 | 2/2003 | Franchini et al. |
| 6,699,997 B2 | 3/2004 | Hildesheim et al. |
| 6,852,337 B2 | 2/2005 | Gabel et al. |
| 7,056,942 B2 * | 6/2006 | Hildesheim et al. ........ 514/411 |
| 7,126,008 B2 | 10/2006 | Hildesheim et al. |
| 2001/0036959 A1 | 11/2001 | Gabel et al. |
| 2001/0036960 A1 | 11/2001 | Decker et al. |
| 2002/0052367 A1 | 5/2002 | Heller |
| 2002/0068740 A1 | 6/2002 | Mylari |
| 2002/0099013 A1 | 7/2002 | Piccariello et al. |
| 2002/0099046 A1 | 7/2002 | Scott |
| 2002/0107279 A1 | 8/2002 | Barone et al. |
| 2002/0115655 A1 | 8/2002 | Mehanna et al. |
| 2002/0143045 A1 | 10/2002 | Hildesheim et al. |
| 2002/0169199 A1 | 11/2002 | Gruber et al. |
| 2003/0004205 A1 | 1/2003 | Gabel et al. |
| 2003/0004206 A1 | 1/2003 | Decker et al. |
| 2003/0035836 A1 | 2/2003 | Shanghvi et al. |
| 2003/0036559 A1 | 2/2003 | Beyer et al. |
| 2003/0050301 A1 | 3/2003 | Mylari |
| 2003/0054041 A1 | 3/2003 | Lemmens et al. |
| 2003/0166702 A1 | 9/2003 | Kor et al. |
| 2004/0019096 A1 | 1/2004 | Oh et al. |
| 2004/0152756 A1 | 8/2004 | Chen et al. |
| 2004/0186158 A1 | 9/2004 | Oh |
| 2004/0220250 A1 | 11/2004 | Oh |
| 2005/0009897 A1 | 1/2005 | Anderson et al. |
| 2005/0148779 A1 | 7/2005 | Oh et al. |

(Continued)

FOREIGN PATENT DOCUMENTS

WO    WO99/05105 A1    2/1999

(Continued)

OTHER PUBLICATIONS

MedlinePlus, Carvedilol, 2007.*

(Continued)

*Primary Examiner*—Kamal A. Saeed
*Assistant Examiner*—Andrew B. Freistein
(74) *Attorney, Agent, or Firm*—Grace C. Hsu; Mary E. McCarthy; Charles M. Kinzig

(57) ABSTRACT

The present invention relates to carvedilol phosphate salts, which include novel crystalline forms of carvedilol dihydrogen phosphate (i.e., dihydrogen phosphate salt of 1-(carbazol-4-yloxy-3-[[2-(o-methoxyphenoxy)ethyl]amino]-2-propanol) and/or carvedilol hydrogen phosphate, etc.), and/or solvates thereof, compositions containing the aforementioned salts and/or solvates, and methods of using the aforementioned salts and/or solvates to treat hypertension, congestive heart failure and angina, etc.

8 Claims, 29 Drawing Sheets

U.S. PATENT DOCUMENTS

2005/0169994 A1 8/2005 Burke et al.

FOREIGN PATENT DOCUMENTS

| WO | WO99/52526 | 10/1999 |
|---|---|---|
| WO | WO00/004902 | 2/2000 |
| WO | WO00/032174 | 6/2000 |
| WO | WO01/74356 | 10/2001 |
| WO | WO 01/87837 | 11/2001 |
| WO | WO01/87837 A1 | 11/2001 |
| WO | WO02/00216 A1 | 1/2002 |
| WO | WO02/092078 | 11/2002 |
| WO | WO03/007962 | 1/2003 |
| WO | WO03/024426 | 3/2003 |
| WO | WO03/024429 | 3/2003 |
| WO | WO03/028645 | 4/2003 |
| WO | WO03/028718 | 4/2003 |
| WO | WO2004/009120 | 1/2004 |
| WO | WO2004/016249 | 2/2004 |
| WO | WO2004/041252 | 5/2004 |
| WO | WO2004/056336 | 7/2004 |
| WO | WO05/051322 | 8/2005 |

OTHER PUBLICATIONS

New Drug Application (NDA) for Coreg CR (carvedilol phosphate) Extended Release Capsules, NDA 22-012 Excerpt, Section m3.2.S.4.5, Justification of Specification, submitted Dec. 21, 2005, Approved Oct. 20, 2006, pp. 3-5.

Chemical & Engineering News, Feb. 24, 2003, pp. 32-35.

Jain et al., "Polymorphism in Pharmacy", Indian Drugs, 23 (6), 1986, pp. 315-329.

U.S. Appl. No. 10/513,234, filed May 3, 2002, inventor Oh.

U.S. Appl. No. 10/513,235, filed Nov. 2, 2004, inventor Oh et al.

U.S. Appl. No. 10/518,206, filed Dec. 16, 2004, inventor Chen at al.

U.S. Appl. No. 10/997,230, filed Nov. 24, 2004, inventor Brook et al.

U.S. Appl. No. 11/137,261 filed May 25, 2005, Burke et al.

* cited by examiner

CARVEDILOL PHOSPHATE SALTS AND/OR SOLVATES THEREOF, CORRESPONDING COMPOSITIONS AND/OR METHODS OF TREATMENT

This application is a National filing under 35 USC 371 of PCT/US03/20408, filed Jun. 27, 2003, which claims the benefit of U.S. Provisional Application No. 60/392,175, filed Jun. 27, 2002.

FIELD OF THE INVENTION

The present invention relates to a salt of carvedilol and/or corresponding solvates thereof, compositions containing such a salt of carvedilol and/or corresponding solvates thereof, and/or methods of using the aforementioned compound(s) in the treatment of certain disease states in mammals, in particular man.

The present invention further relates to carvedilol phosphate salts, which include novel crystalline forms of carvedilol dihydrogen phosphate (i.e., such as dihydrogen phosphate salt of 1-(carbazol-4-yloxy-3-[[2-(o-methoxyphenoxy)ethyl]amino]-2-propanol), carvedilol hydrogen phosphate,etc.), and/or other corresponding solvates thereof, compositions containing such salts and/or solvates, and methods of using the aformentioned compounds to treat hypertension, congestive heart failure and angina, etc.

BACKGROUND OF THE INVENTION

The compound, 1-(carbazol-4-yloxy-3-[[2-(o-methoxyphenoxy)ethyl]-amino]-2-propanol is known as Carvedilol. Carvedilol is depicted by the following chemical structure:

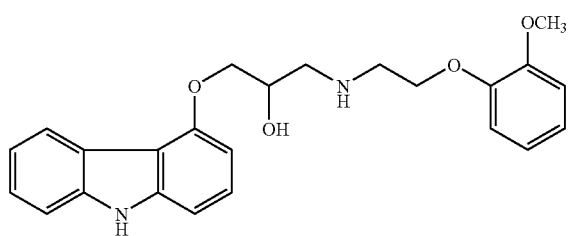

Carvedilol is disclosed in U.S. Pat. No. 4,503,067 to Wiedemann et al. (i.e., assigned to Boehringer Mannheim, GmbH, Mannheim-Waldhof, Fed. Rep. of Germany), which was issued on Mar. 5, 1985.

Currently, carvedilol is synthesized as free base for incorporation in medication that is available commercially. The aforementioned free base form of Carvedilol is a racemic mixture of R(+) and S(−) enantiomers, where nonselective β-adrenoreceptor blocking activity is exhibited by the S(−) enantiomer and α-adrenergic blocking activity is exhibited by both R(+) and S(−) enantiomers. Those unique features or characteristics associated with such a racemic Carvedilol mixture contributes to two complementary pharmacologic actions: i.e., mixed venous and arterial vasodilation and non-cardioselective, beta-adrenergic blockade.

Carvedilol is used for treatment of hypertension, congestive heart failure and angina. The currently commercially available carvedilol product is a conventional, tablet prescribed as a twice-a-day (BID) medication in the United States.

Carvedilol contains an α-hydroxyl secondary amine functional group, which has a pKa of 7.8. Carvedilol exhibits predictable solubility behaviour in neutral or alkaline media, i.e. above a pH of 9.0, the solubility of carvedilol is relatively low (<1 μg/mL). The solubility of carvedilol increases with decreasing pH and reaches a plateau near pH=5, i.e. where saturation solubility is about 23 μg/mL at pH=7 and about 100 μg/mL at pH=5 at room temperature. At lower pH values (i.e., at a pH of 1 to 4 in various buffer systems), solubility of carvedilol is limited by the solubility of its protonated form or its corresponding salt formed in-situ. The hydrochloride salt of carvedilol generated in situ in acidic medium, which simulates gastric fluid, is less soluble in such medium.

In light of the foregoing, a salt, and/or novel crystalline form of carvedilol with greater aqueous solubility, chemical stability, etc. would offer many potential benefits for provision of medicinal products containing the drug carvedilol. Such benefits would include products with the ability to achieve desired or prolonged drug levels in a systemic system by sustaining absorption along the gastro-intestinal tract of mammals (i.e., such as humans), particularly in regions of neutral pH, where a drug, such as carvedilol, has minimal solubility.

Surprisingly, it has now been shown that a novel crystalline form of carvedilol phosphate salt (i.e., such as carvedilol dihydrogen phosphate and/or carvedilol hydrogen phosphate, etc.) can be isolated as a pure, crystalline solid, which exhibits much higher aqueous solubility than the corresponding free base or other prepared crystalline salts of carvedilol, such as the hydrochloride salt. This novel crystalline form also has potential to improve the stability of carvedilol in formulations due to the fact that the secondary amine functional group attached to the carvedilol core structure, a moiety pivotal to degradation processes, is protonated as a salt.

In light of the above, a need exists to develop different carvedilol forms and/or different compositions, respectively, which have greater aqueous solubility, chemical stability, sustained or prolonged drug or absorption levels (i.e., such as in neutral gastrointestinal tract pH regions, etc.).

There also exists a need to develop methods of treatment for hypertension, congestive heart failure or angina, etc. which comprises administration of the aforementioned carvedilol phosphate salts and/or solvates thereof or corresponding pharmaceutical compositions, which contain such salts, and/or solvates.

The present invention is directed to overcoming these and other problems encountered in the art.

SUMMARY OF THE INVENTION

The present invention relates to a salt of carvedilol and/or corresponding solvates thereof, compositions containing such carvedilol and/or corresponding solvates thereof, and/or methods of using the aforementioned compound(s) in the treatment of certain disease states in mammals, in particular man.

The present invention further relates to carvedilol phosphate salts, which include novel crystalline forms of carvedilol phosphate (i.e., such as dihydrogen phosphate salt of 1-(carbazol-4-yloxy-3-[[2-(o-methoxyphenoxy)ethyl] amino]-2-propanol), carvedilol hydrogen phosphate,etc.), and/or other-corresponding solvates thereof.

The present invention relates to a pharmaceutical composition, which contains carvedilol phosphate salts and/or solvates thereof.

The present invention further relates to a method of treating hypertension, congestive heart failure and angina, which comprises administering to a subject in need thereof an effective amount of a carvedilol phosphate salt (which include novel crystalline forms) and/or solvates thereof or a pharmaceutical composition (i.e., which contains such salts and/or solvates of carvedilol phosphate), etc.

BRIEF DESCRIPTION OF THE INVENTION

DETAILED DESCRIPTION OF THE INVENTION

The present invention relates to a salt of carvedilol and/or corresponding solvates thereof, compositions containing such carvedilol salts and/or corresponding solvates thereof, and/or methods of using the aforementioned compound(s) in the treatment of certain disease states in mammals, in particular man.

The present invention further relates to carvedilol phosphate salts, which include novel crystalline forms of carvedilol dihydrogen phosphate (i.e., such as dihydrogen phosphate salt of 1-(carbazol-4-yloxy-3-[[2-(o-methoxyphenoxy)ethyl]amino]-2-propanol), carvedilol hydrogen phosphate,etc.) and/or other carvedilol phosphate solvates thereof.

The present invention relates to a pharmaceutical composition, which contains carvedilol phosphate salts and/or solvates thereof.

The present invention further relates to a method of treating hypertension, congestive heart failure and angina, which comprises administering to a subject in need thereof an effective amount of a carvedilol phosphate salt (which include novel crystalline forms), and/or solvates thereof or a pharmaceutical composition (i.e., which contains such salts and/or solvates of carvedilol phosphate), etc.

Carvedilol is disclosed and claimed in U.S. Pat. No. 4,503,067 to Wiedemann et al. ("U.S. '067 Patent"). Reference should be made to U.S. '067 Patent for its full disclosure, which include methods of preparing and/or using the carvedilol compound, etc. The entire disclosure of the U.S. '067 Patent is incorporated hereby by reference in its entirety.

The present invention relates to a compound, which is a salt and/or novel crystalline forms of carvedilol phosphate (i.e., which include crystalline forms of carvedilol dihydrogen phosphate, carvedilol hydrogen phosphate, etc.) and/or solvates of carvedilol phosphate (i.e., which include carvedilol dihydrogen phosphate hemihydrate, carvedilol dihydrogen phosphate dihydrate (i.e., such as Forms II and IV, respectively, etc.), and/or carvedilol dihydrogen phosphate methanol solvate, etc.)

In accordance with the present invention, it has been unexpectedly found that carvedilol dihydrogen phosphate can be isolated readily as novel crystalline forms, which displays much higher solubility when compared to the free base of carvedilol. An example in the present invention of a novel carvedilol phosphate salt is a novel crystalline form of carvedilol dihydrogen phosphate (i.e., identified as the dihydrogen phosphate salt of 1-(carbazol-4-yloxy-3-[[2-(o-methoxyphenoxy)ethyl]amino]-2-propanol).

Figure 9:
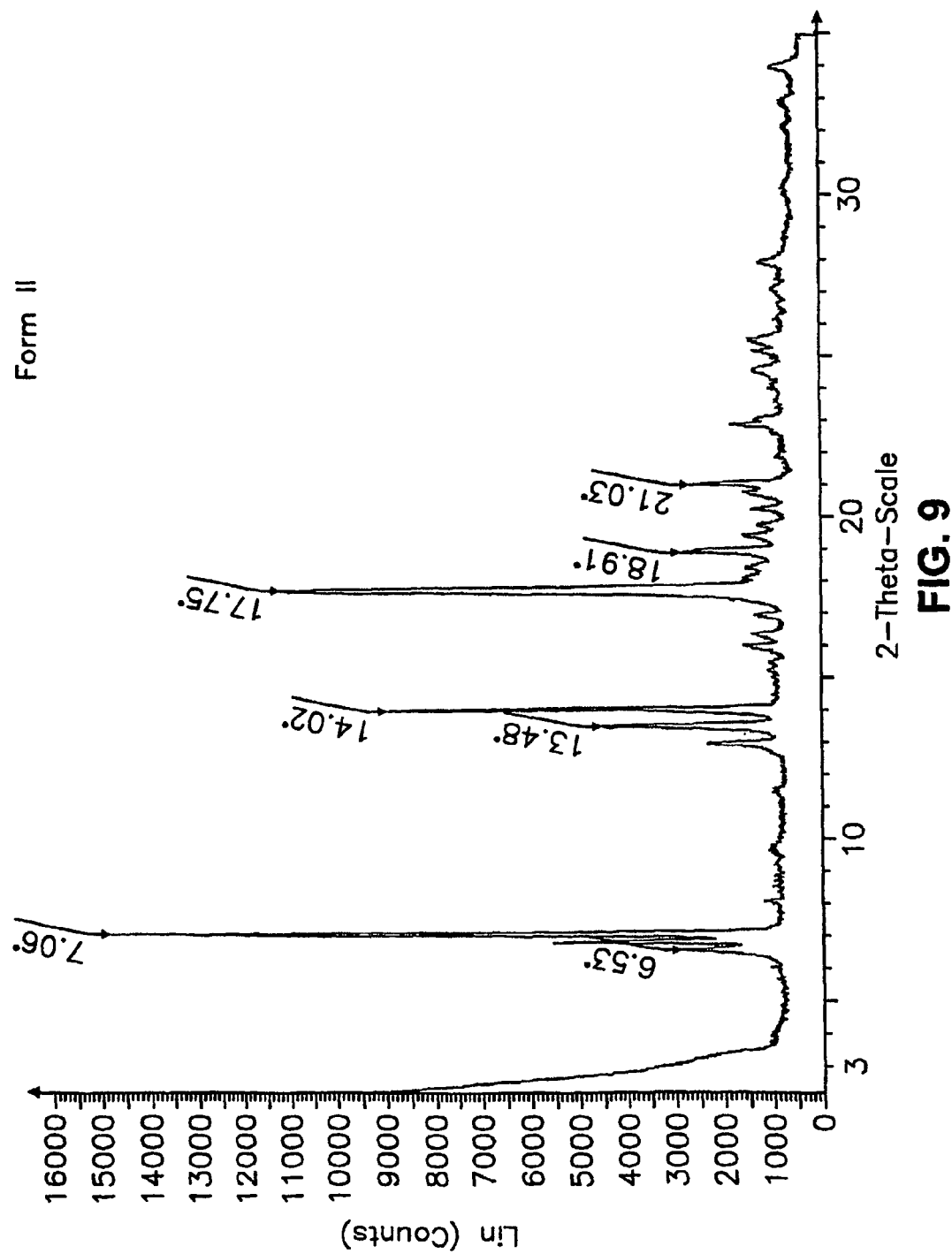
FIG. 9 is an x-ray powder diffractogram for carvedilol dihydrogen phosphate dihydrate (Form II).
Figure 10:
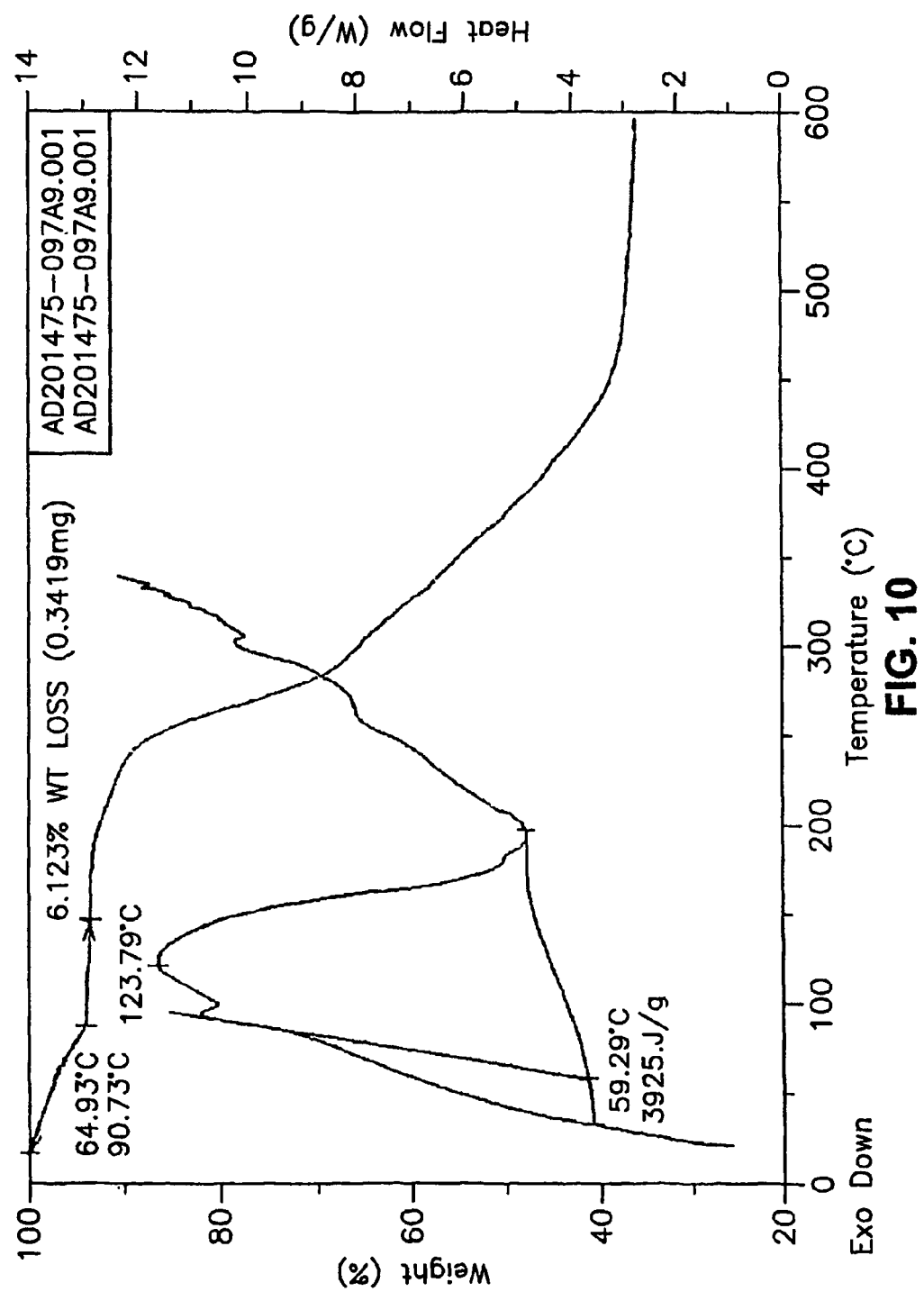
FIG. 10 shows the thermal analysis results for carvedilol dihydrogen phosphate dihydrate (Form II).
Figure 11:
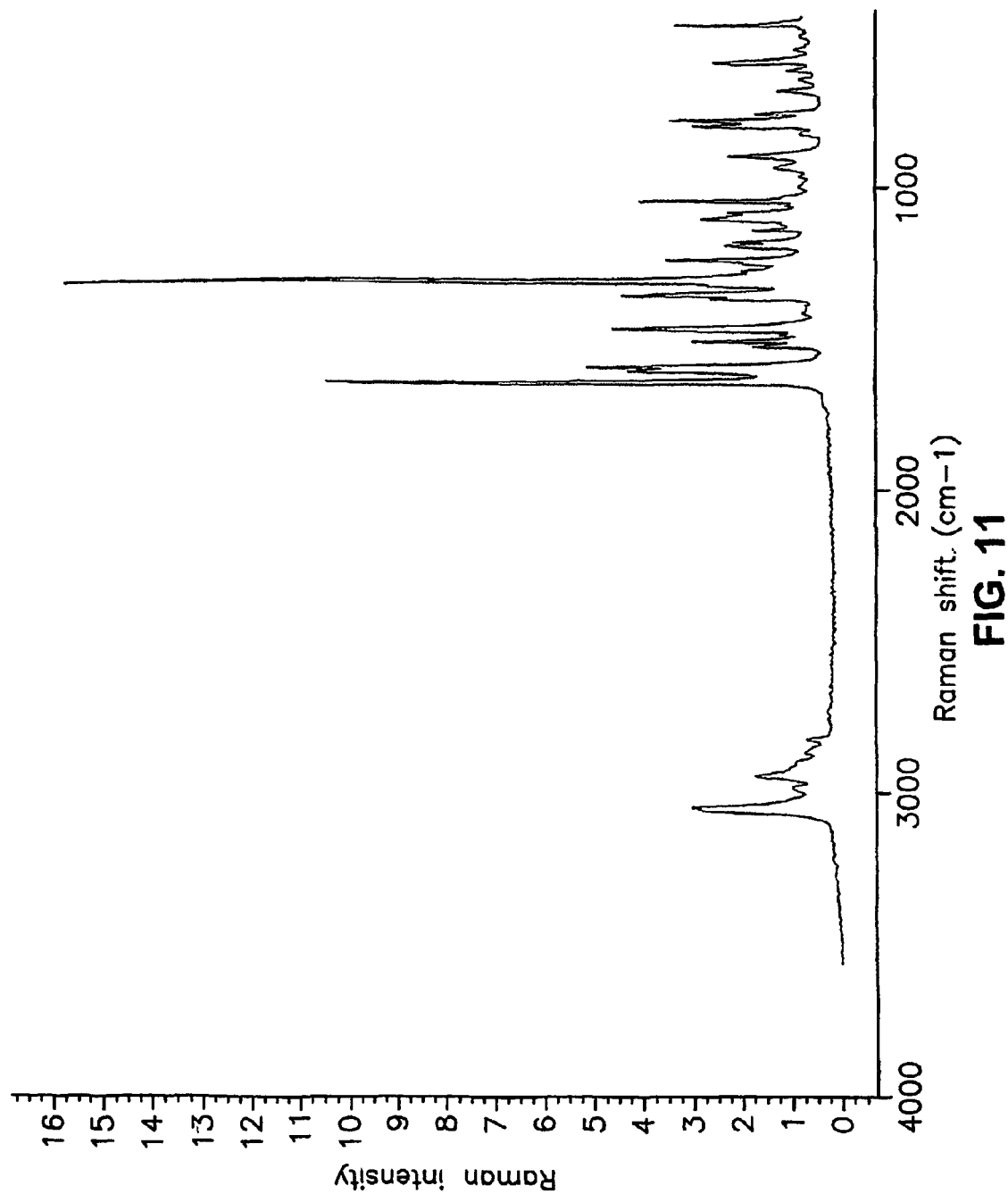
FIG. 11 is an FT-Raman spectrum for carvedilol dihydrogen phosphate dihydrate (Form II).
Figure 12:
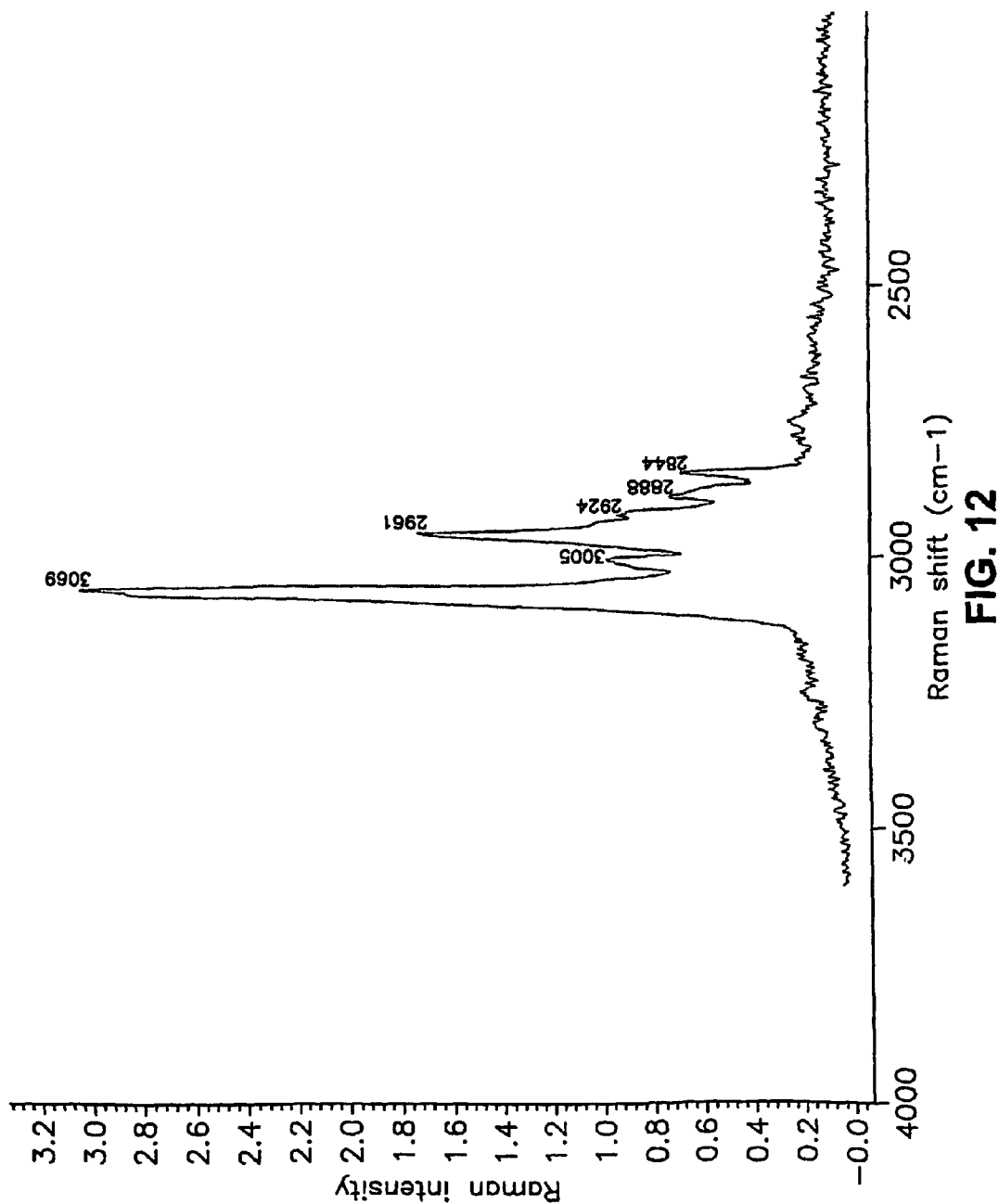
FIG. 12 is an FT-Raman spectrum for carvedilol dihydrogen phosphate dihydrate in the 4000-2000 $cm^{-1}$ region of the spectrum (Form II).
Figure 13:
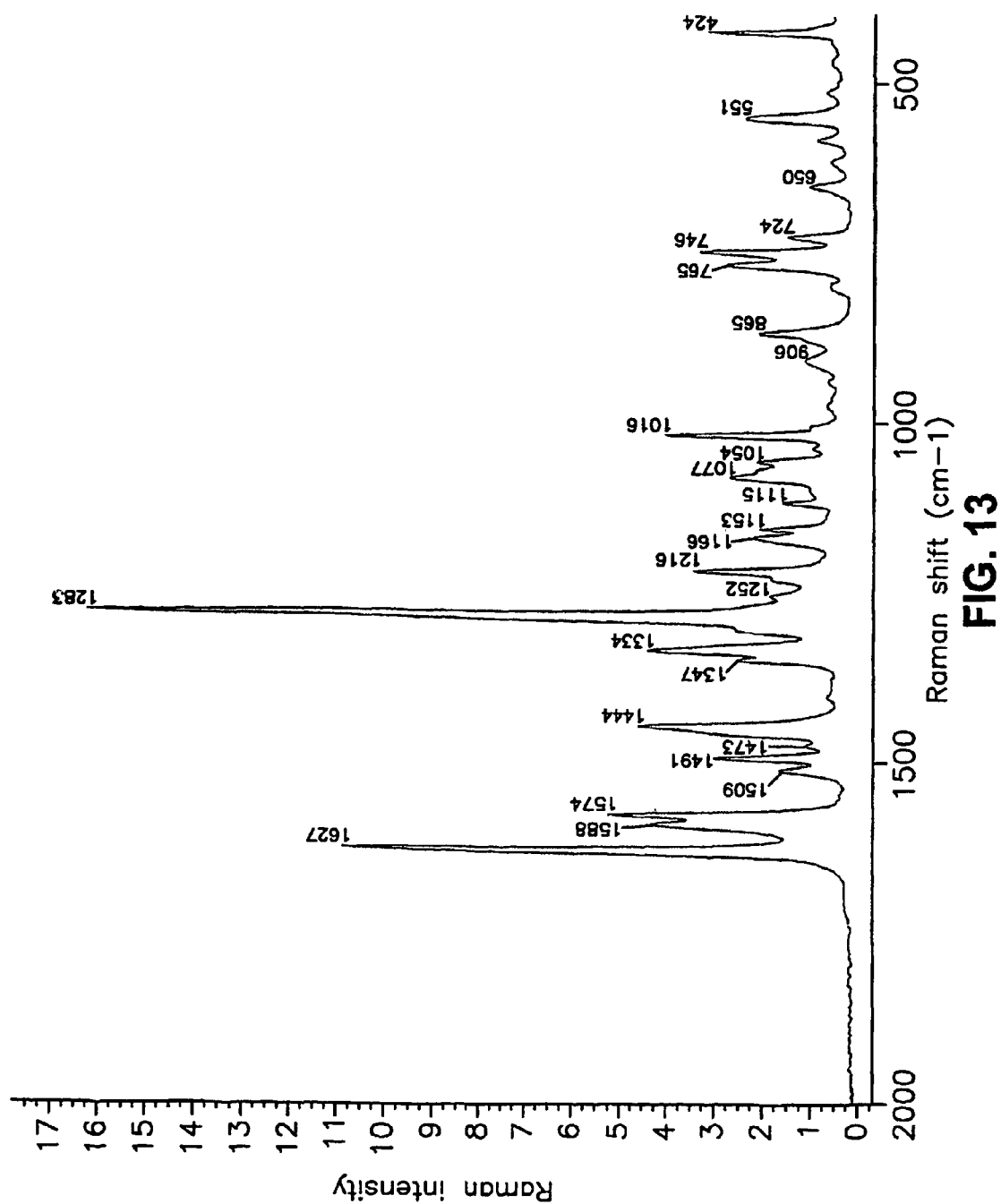
FIG. 13 is an FT-Raman spectrum for carvedilol dihydrogen phosphate dihydrate in the 2000-400 $cm^{-1}$ region of the spectrum (Form II).
Figure 14:
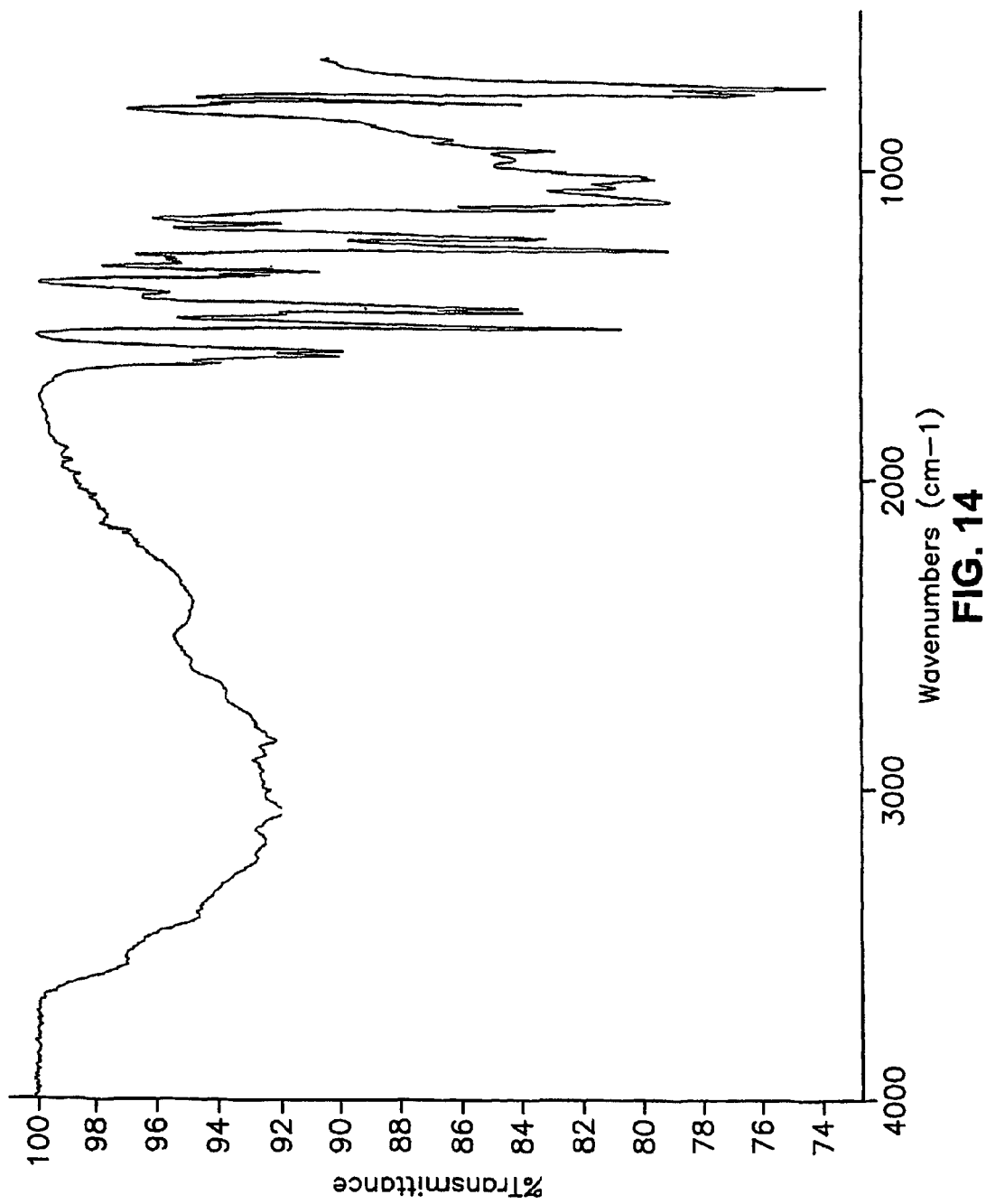
FIG. 14 is an FT-IR spectrum for carvedilol dihydrogen phosphate dihydrate (Form II).
Figure 15:
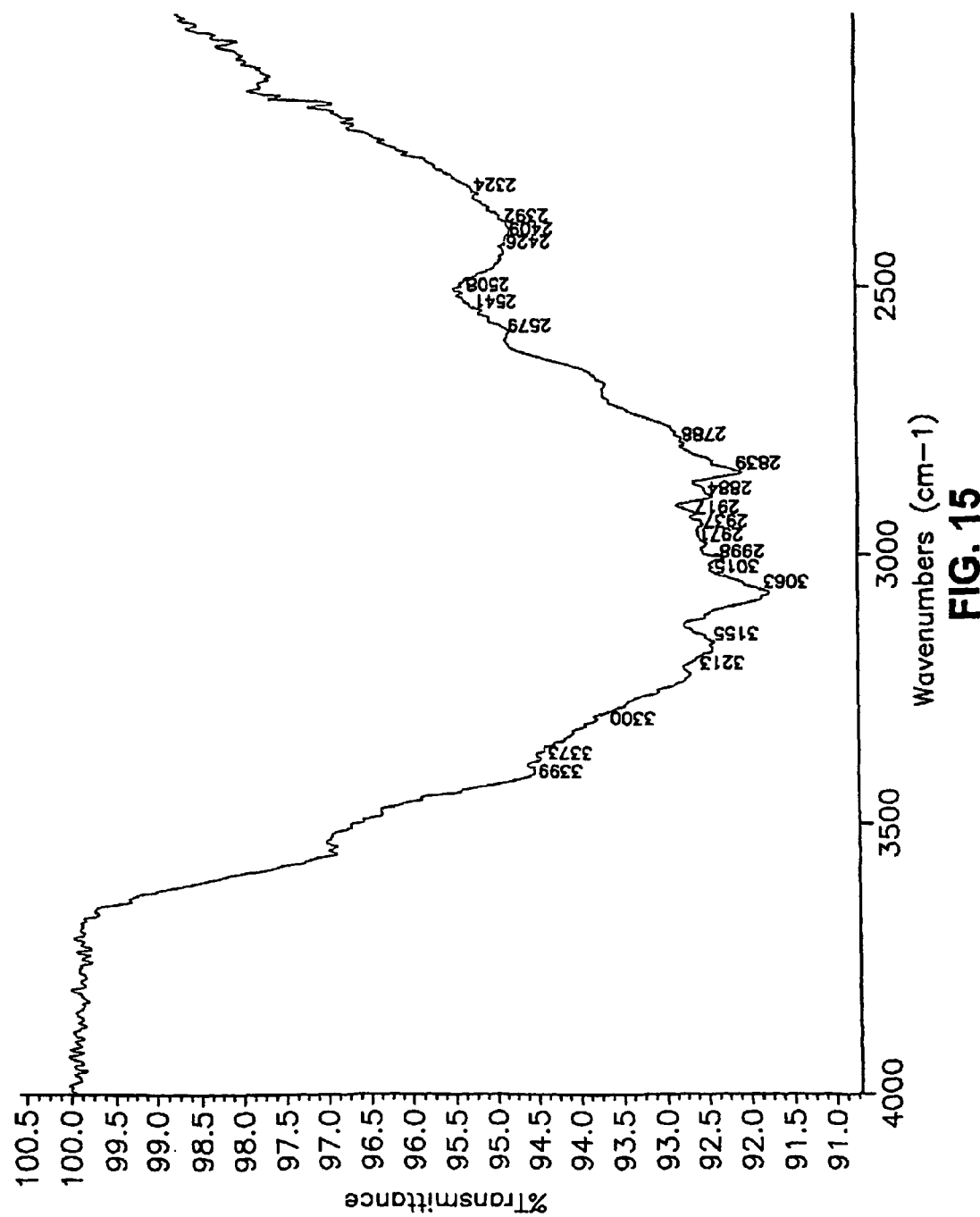
FIG. 15 is an FT-IR spectrum for carvedilol dihydrogen phosphate dihydrate in the 4000-2000 $cm^{-1}$ region of the spectrum (Form II).
Figure 16:
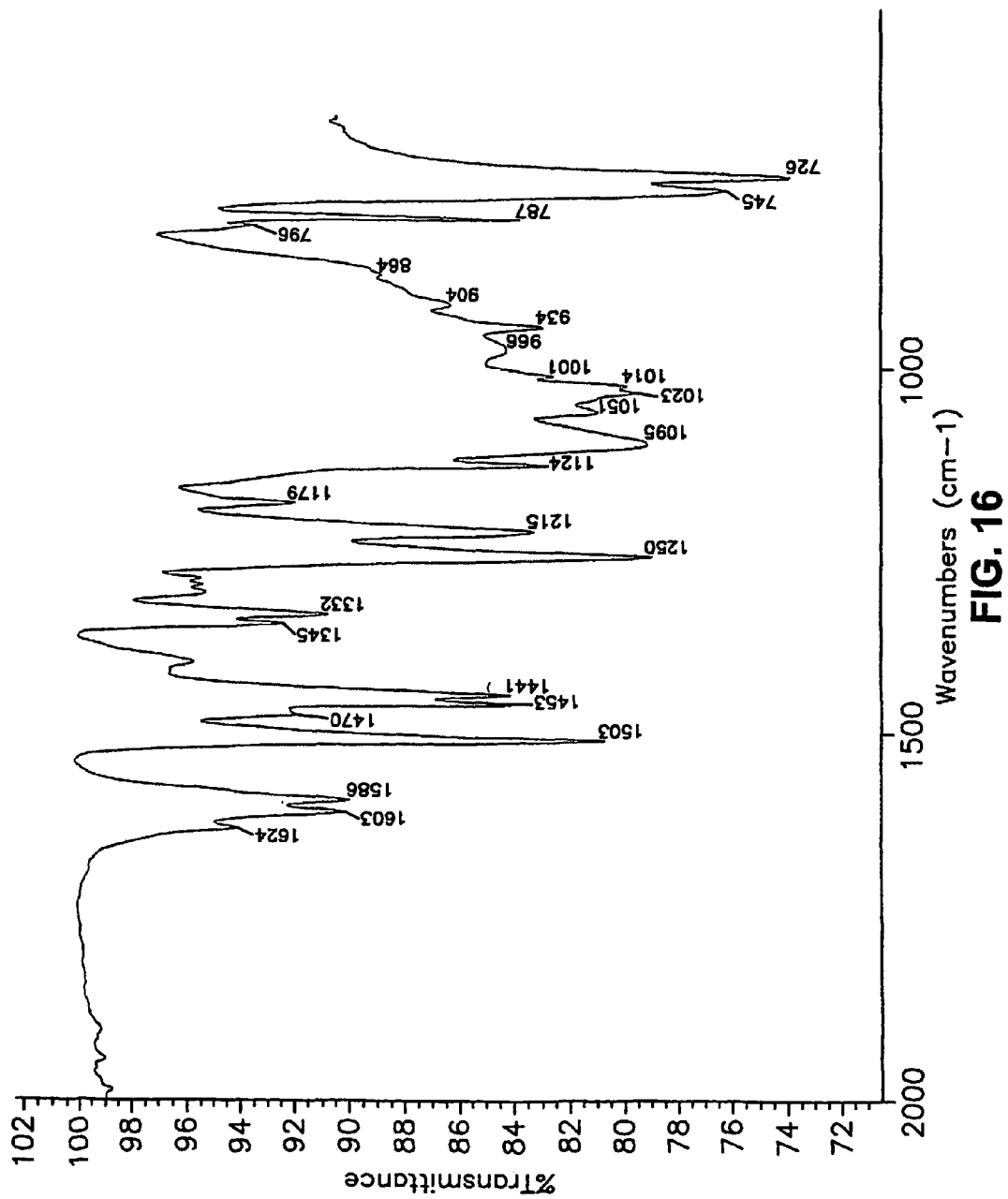
FIG. 16 is an FT-IR spectrum for carvedilol dihydrogen phosphate dihydrate in the 2000-500 $cm^{-1}$ region of the spectrum (Form II).
Figure 17:
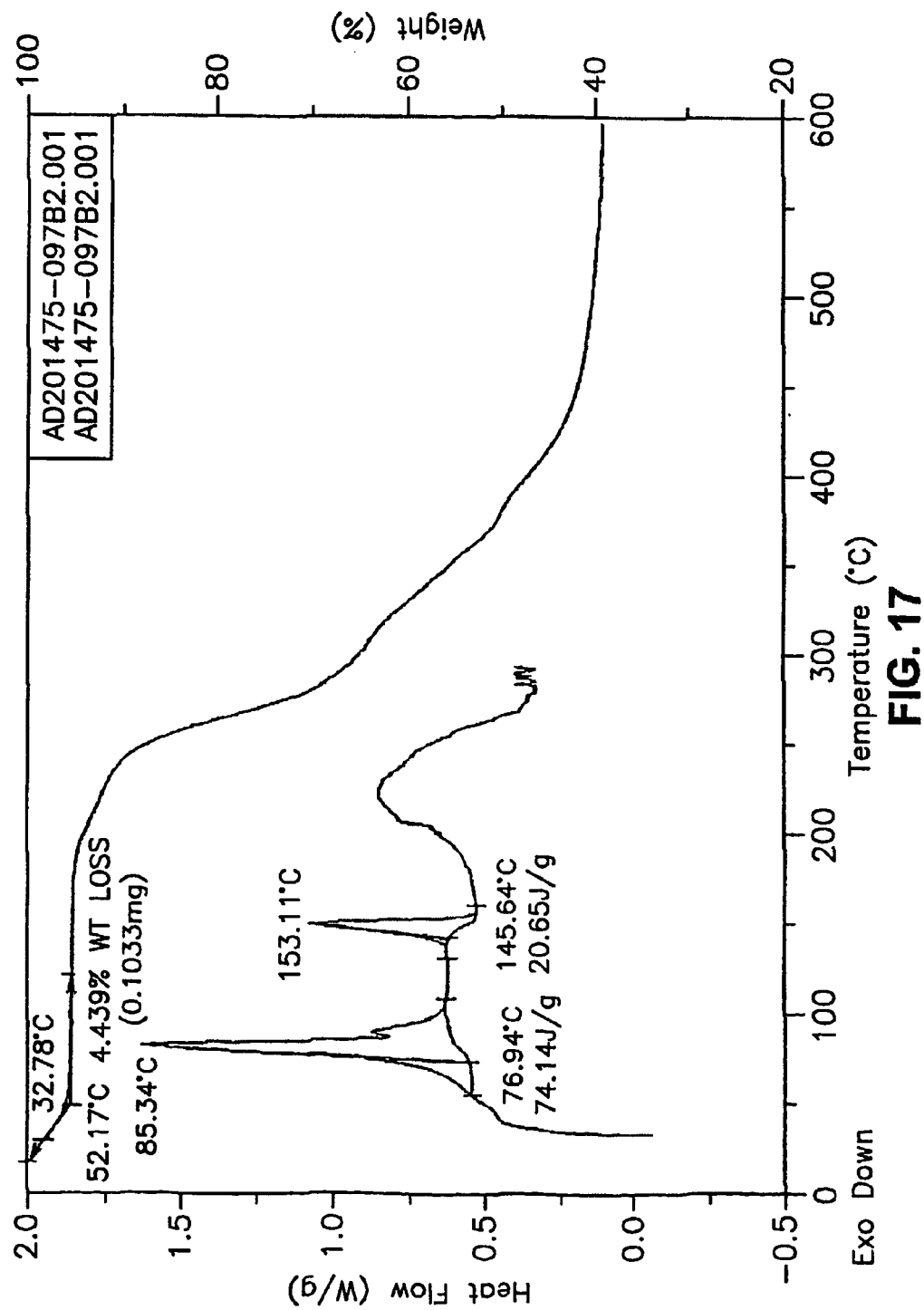
FIG. 17 shows the thermal analysis results for carvedilol dihydrogen phosphate methanol solvate (Form III).
Figure 18:
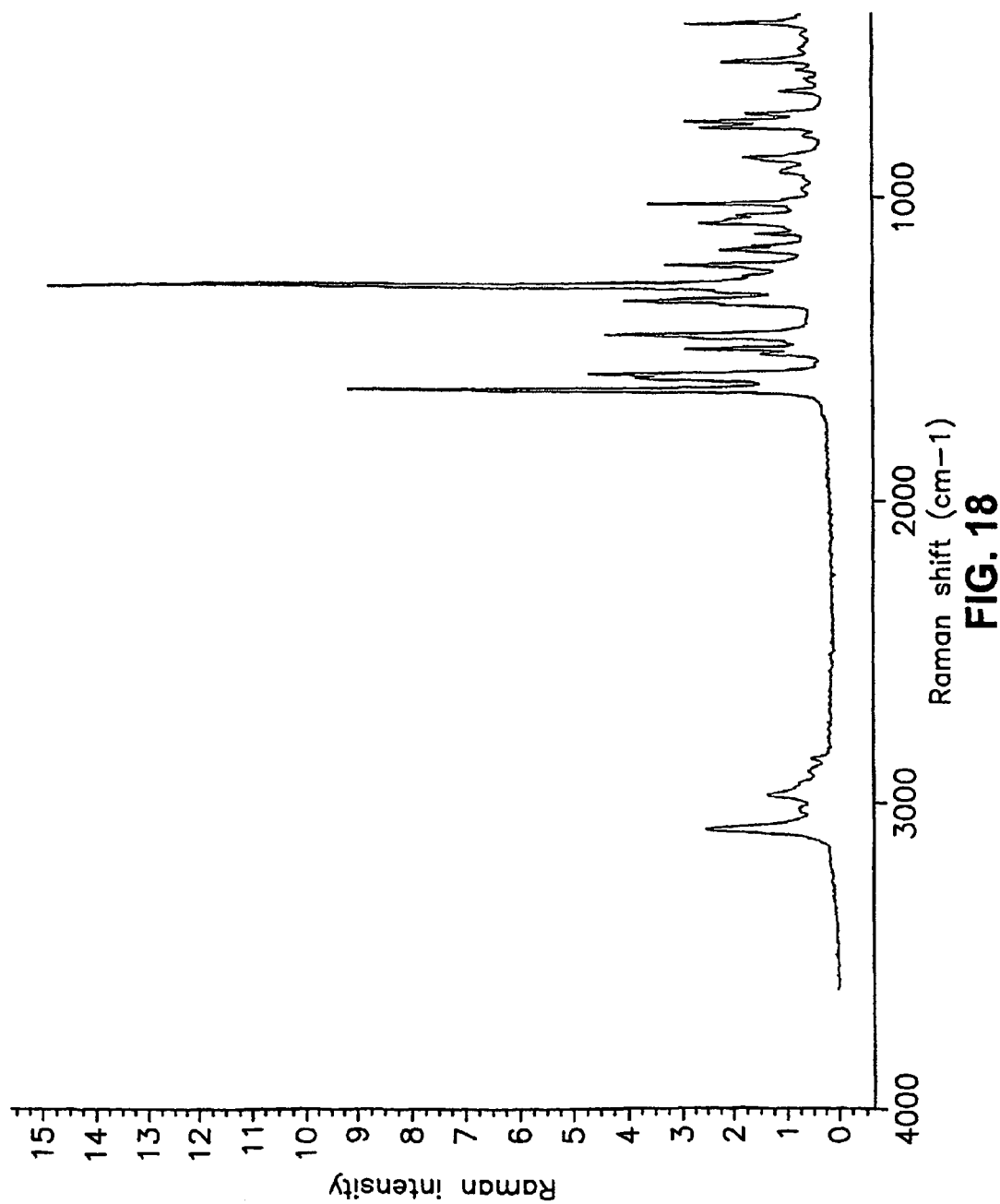
FIG. 18 is an FT-Raman spectrum for carvedilol dihydrogen phosphate methanol solvate (Form II).
Figure 19:
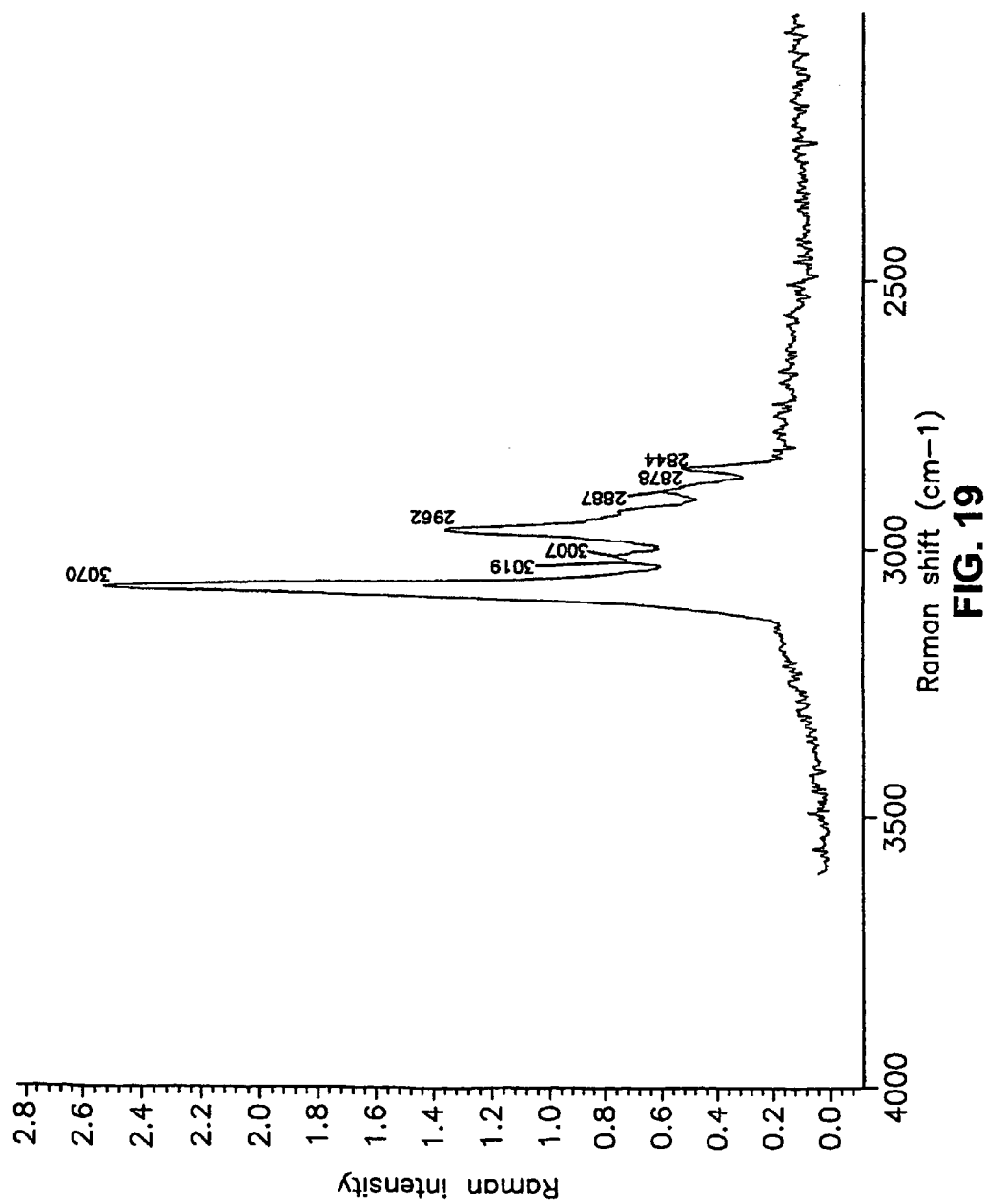
FIG. 19 is an FT-Raman spectrum for carvedilol dihydrogen phosphate methanol solvate in the 4000-2000 $cm^{-1}$ region of the spectrum (Form II).
Figure 20:
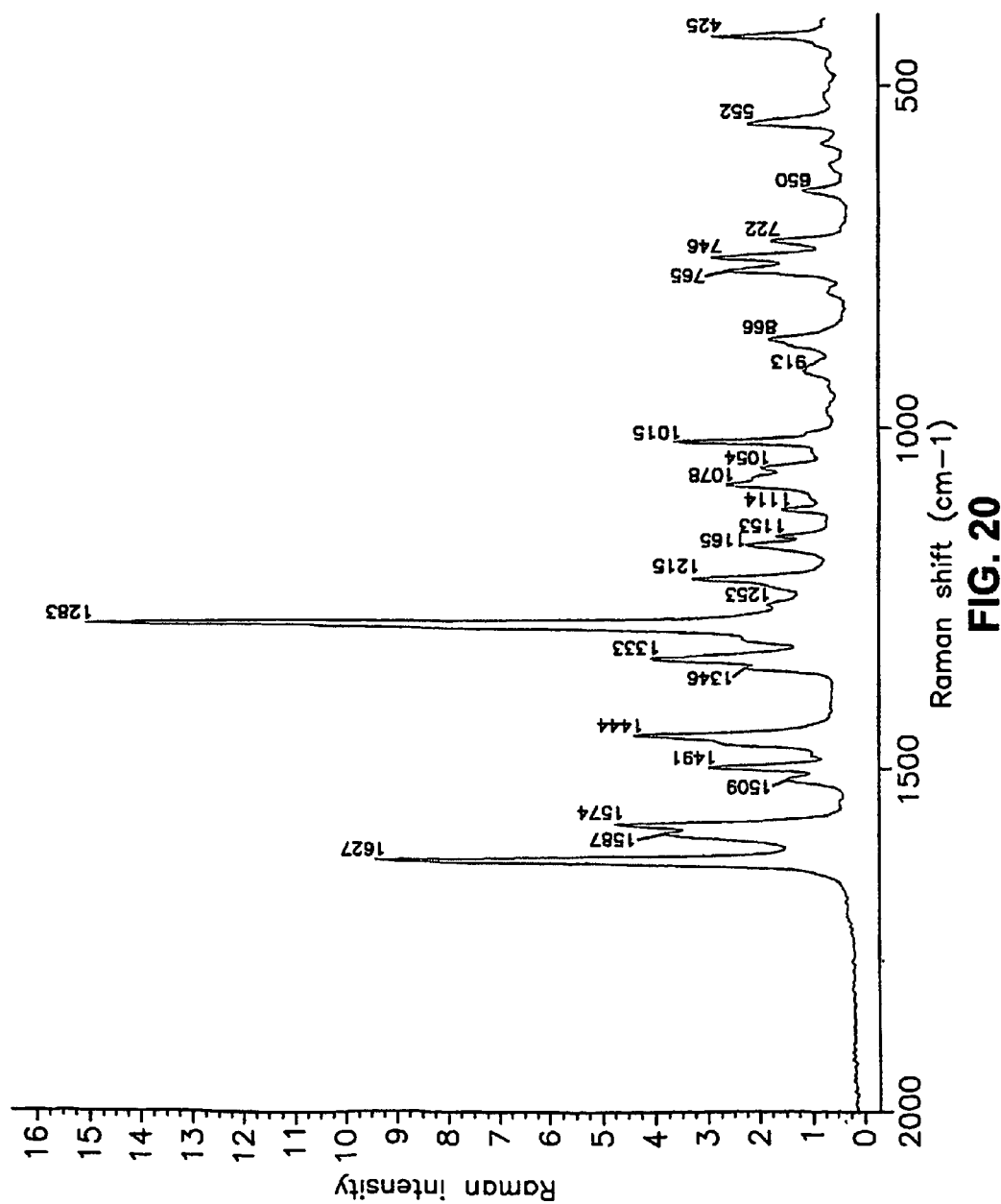
FIG. 20 is an FT-Raman spectrum for carvedilol dihydrogen phosphate methanol solvate in the 2000-400 $cm^{-1}$ region of the spectrum (Form II).
Figure 21:
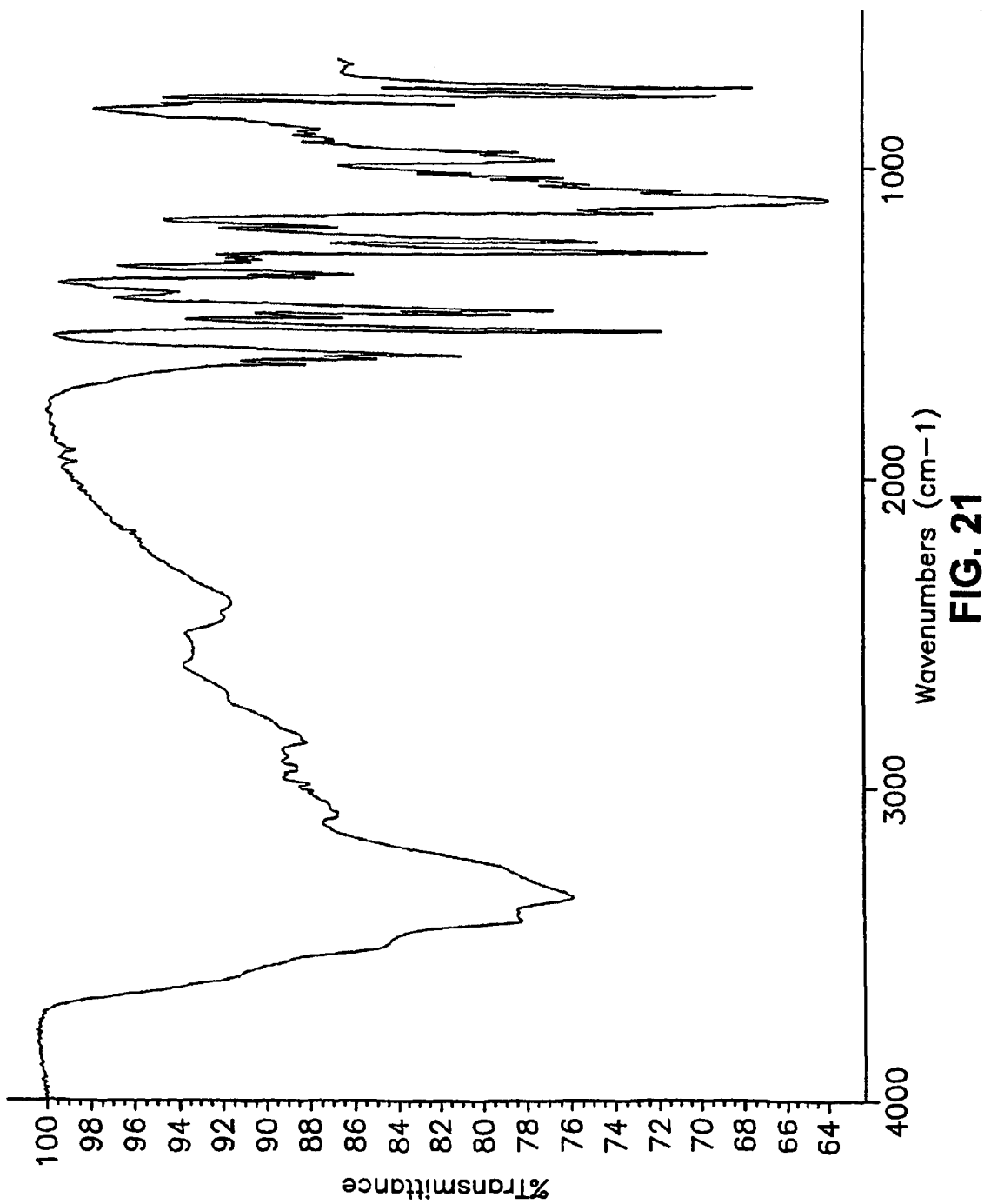
FIG. 21 is an FT-IR spectrum for carvedilol dihydrogen phosphate methanol solvate (Form II).
Figure 22:
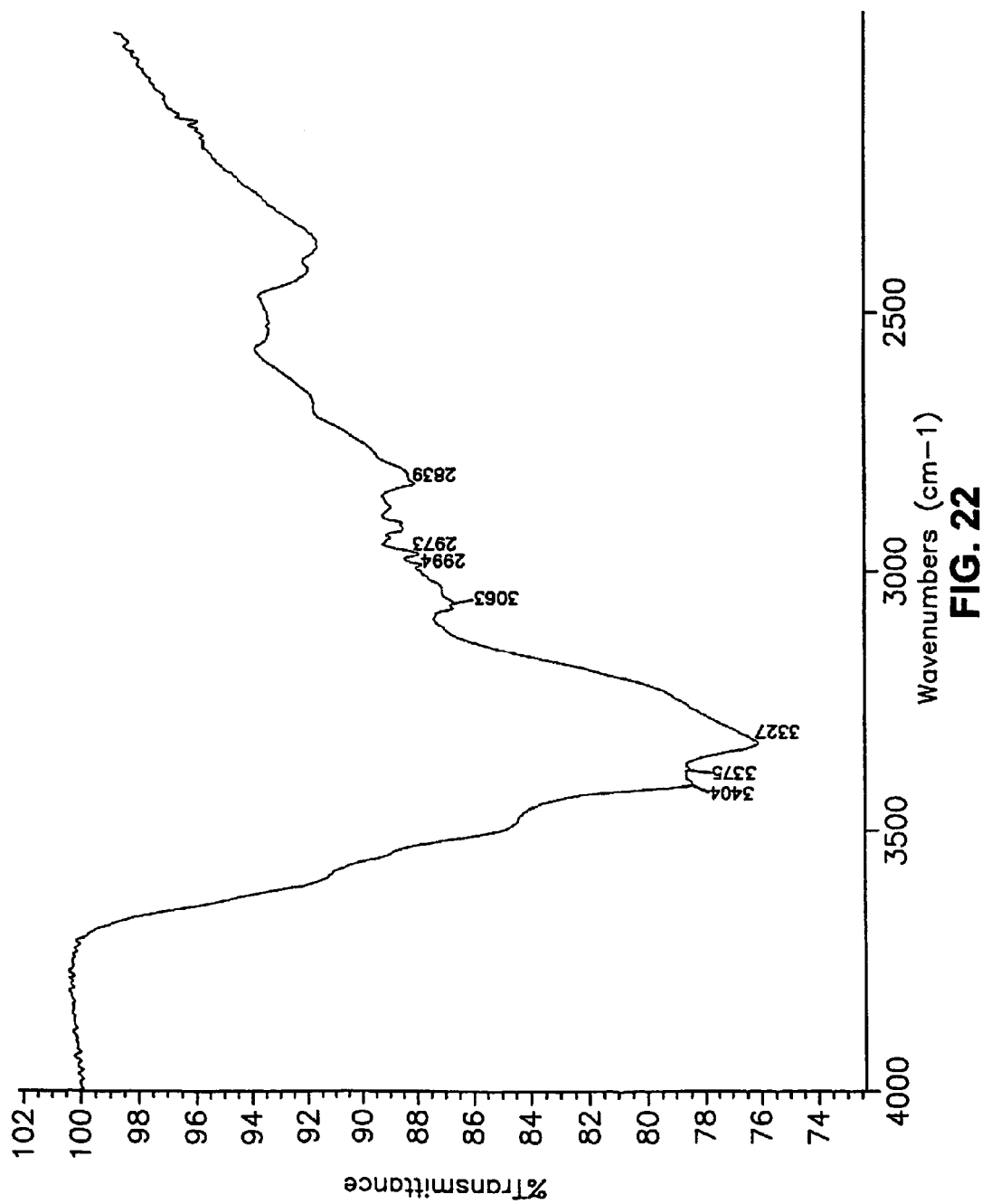
FIG. 22 is an FT-IR spectrum for carvedilol dihydrogen phosphate methanol solvate in the 4000-2000 $cm^{-1}$ region of the spectrum (Form III).
Figure 23:
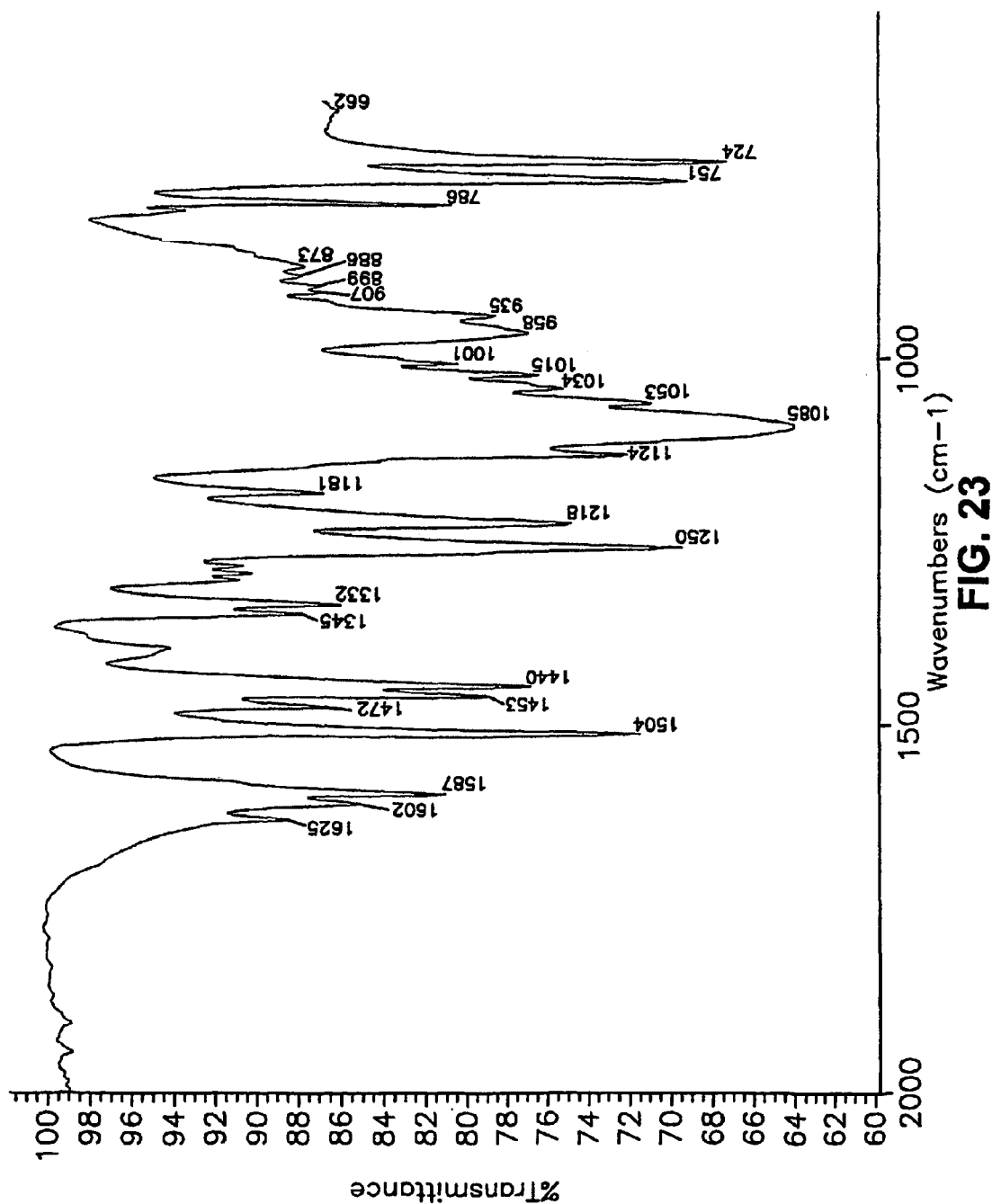
FIG. 23 is an FT-IR spectrum for carvedilol dihydrogen phosphate methanol solvate in the 2000-500 $cm^{-1}$ region of the spectrum (Form II).
Figure 24:
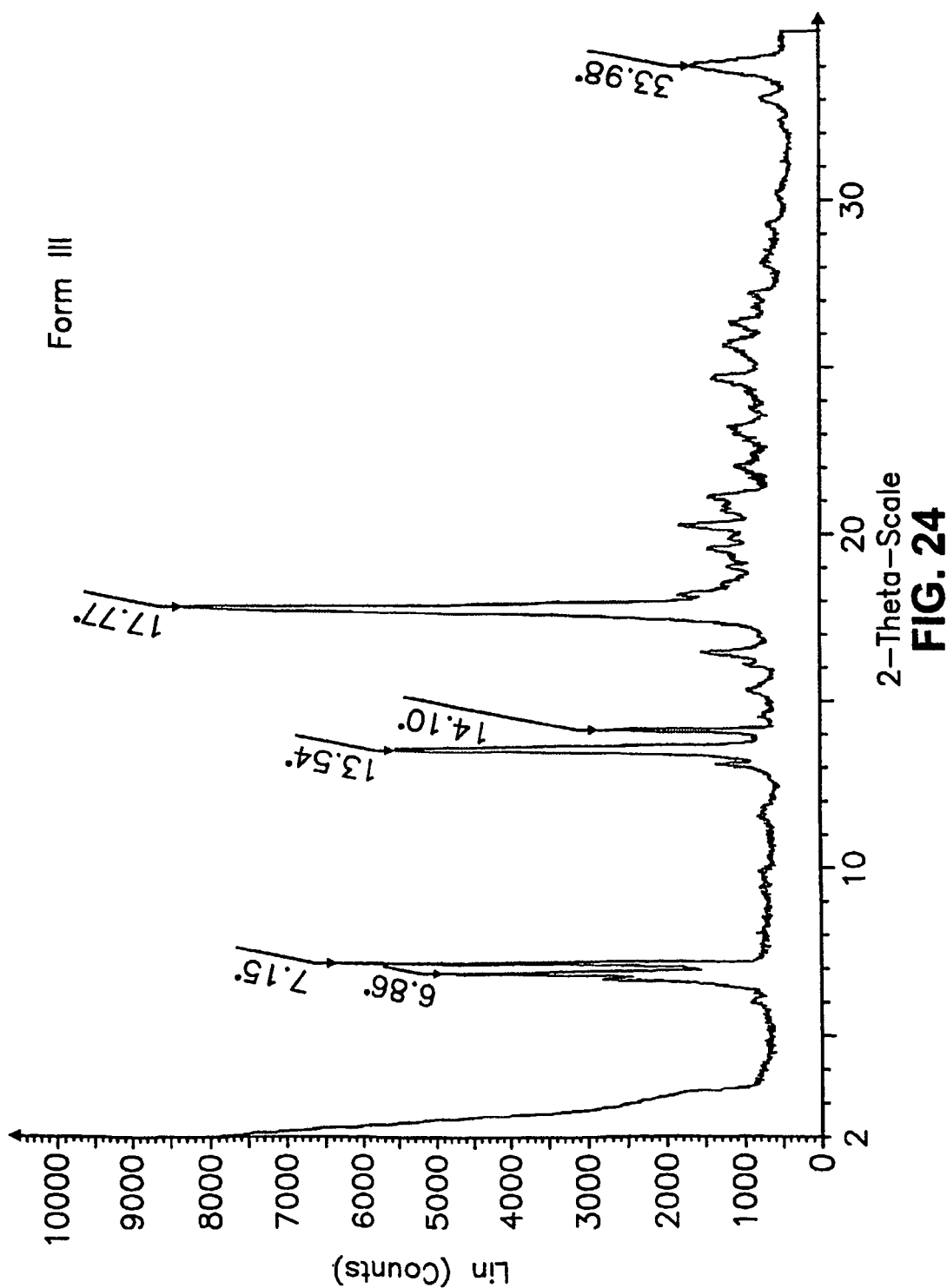
FIG. 24 is an x-ray powder diffractogram for carvedilol dihydrogen phosphate methanol solvate (Form III).
Figure 25:
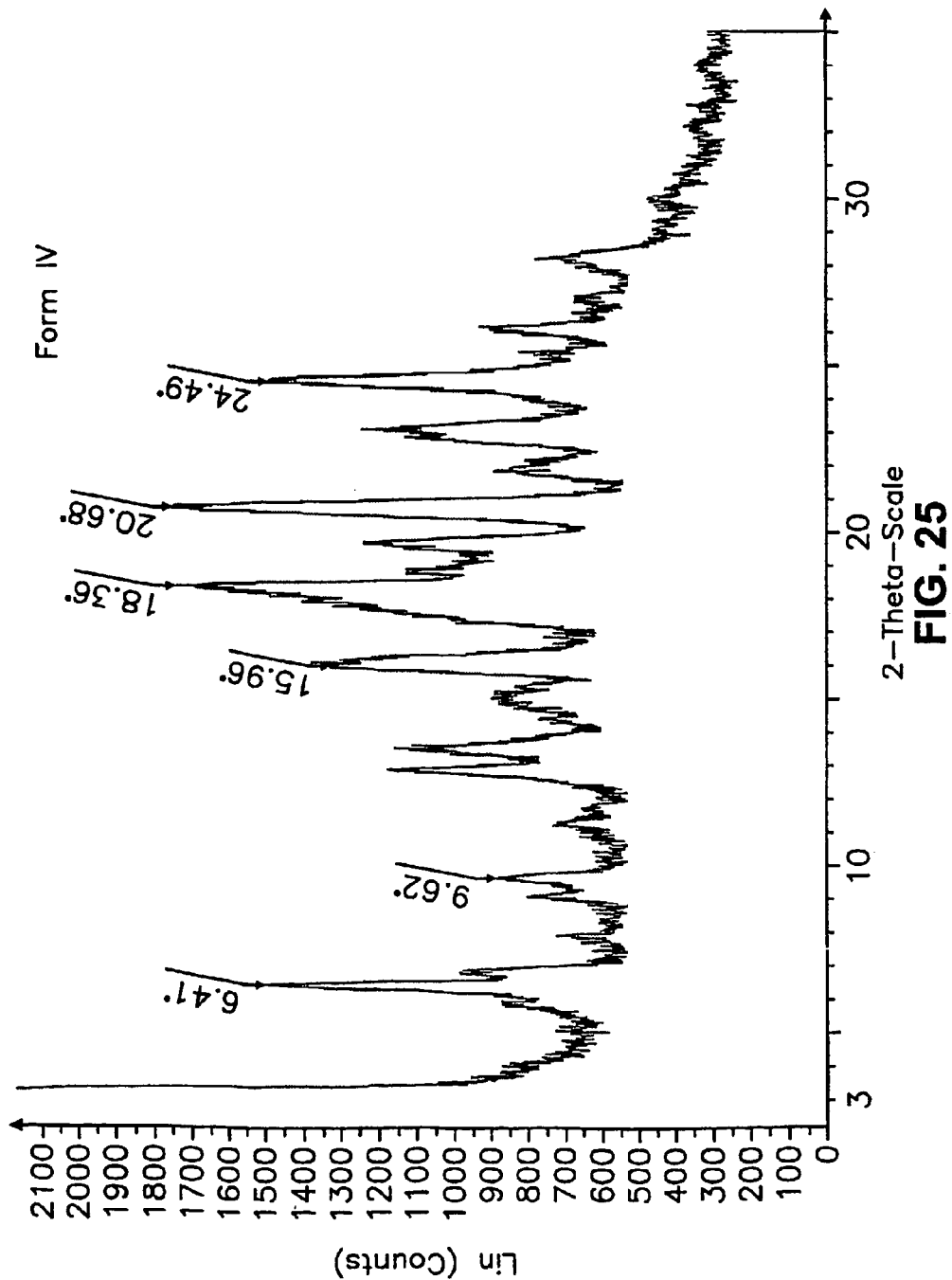
FIG. 25 is an x-ray powder diffractogram for carvedilol dihydrogen phosphate dihydrate (Form IV).

In accordance with the present invention, other carvedilol phosphate salts, and/or solvates of the present invention may be isolated as different solid and/or crystalline forms. Moreover, a specific identified species of a carvedilol phosphate salt (or a specific identified corresponding solvate species) also may also be isolated in various different crystalline or solid forms. For example, carvedilol dihydrogen phosphate, may be isolated in two different and distinct crystalline forms, Forms II and IV (see, Examples 2 and 4), respectively represented and substantially shown FIGS. 9 to 6 (for Form II) and FIG. 25 (for Form IV), which are represent spectroscopic and/or other characterizing data.

It is recognized that the compounds of the present invention may exist in forms as stereoisomers, regioisomers, or diastereiomers, etc. These compounds may contain one or more asymmetric carbon atoms and may exist in racemic and optically active forms. For example, carvedilol may exist as as racemic mixture of R(+) and S(−) enantiomers, or in separate respectively optically forms, i.e., existing separately as either the R(+) enantiomer form or in the S(+) enantiomer form. All of these individual compounds, isomers, and mixtures thereof are included within the scope of the present invention.

Suitable solvates of carvedilol phosphate as defined in the present invention, include, but are not limited to carvedilol dihydrogen phosphate hemihydrate, carvedilol dihydrogen phosphate dihydrate (i.e., which include Forms II and IV, respectively), carvedilol dihydrogen phosphate methanol solvate, and carvedilol hydrogen phosphate, etc.

In particular, crystalline carvedilol dihydrogen phosphate hemihydrate of the instant invention can be prepared by crystallization from an acetone-water solvent system containing carvedilol and $H_3PO_4$.

In accordance with the present invention suitable, solvates of the present invention may be prepared by preparing a slurrying a carvedilol phosphate salt, such as a carvedilol dihydrogen salt, in a solvent, such as methanol.

According to the instant invention, the various forms of carvedilol dihydrogen phosphate (i.e. which include salts and/or solvates thereof) are distinguished from each other using different characterization or identification techniques. Such techniques, include solid state $^{13}C$ Nuclear Magnetic Resonance (NMR), $^{31}P$ Nuclear Magnetic Resonance (NMR), Infrared (IR), Raman, X-ray powder diffraction, etc. and/or other techniques, such as Differential Scanning Calorimetry (DSC) (i.e., which measures the amount of energy (heat) absorbed or released by a sample as it is heated, cooled or held at constant temperature).

In general, the aforementioned solid state NMR techniques are non-destructive techniques to yield spectra, which depict an NMR peak for each magnetically non-equivalent carbon site the solid-state For example, in identification of compounds of the present invention, $^{13}C$ NMR spectrum of a powdered microcrystalline organic molecules reflect that the number of peaks observed for a given sample will depend on the number of chemically unique carbons per molecule and the number of non-equivalent molecules per unit cell. Peak positions (chemical shifts) of carbon atoms reflect the chemical environment of the carbon in much the same manner as in solution-state $^{13}C$ NMR. Although peaks can overlap, each peak is in principle assignable to a single type of carbon. Therefore, an approximate count of the number of carbon sites observed yields useful information about the crystalline phase of a small organic molecule.

Based upon the foregoing, the same principles apply to phosphorus, which has additional advantages due to high sensitivity of the $^{31}P$ nucleus.

Polymorphism also can be studied by comparison of $^{13}C$ and $^{31}P$ spectra. In the case of amorphous material, broadened peak shapes are usually observed, reflecting the range of environments experienced by the $^{13}C$ or $^{31}P$ sites in amorphous material types.

Specifically. carvedilol dihydrogen phosphate salts, hydrates, and/or solvates thereof, substantially shown by the data described in FIGS. 1-29.

For example, crystalline carvedilol dihydrogen phosphate hemihydrate (see, Example 1: Form I) is identified by an x-ray diffraction pattern as shown substantially in FIG. 1, which depicts characteristic peaks in degrees two-theta (2θ): i.e., 7.0±0.2 (2θ), 11.4±0.2 (2θ), 15.9±0.2 (2θ), 18.8±0.2 (2θ), 20.6±0.2 (2θ), 22.8±0.2 (2θ), and 25.4±0.2 (2θ).

Crystalline carvedilol dihydrogen phosphate dihydrate (see, Example 2: Form II) is identified by an x-ray diffraction pattern as shown substantially in FIG. 9, which depicts characteristic peaks in degrees two-theta (2θ): i.e., 6.5±0.2 (2θ), 7.1±0.2 (2θ), 13.5±0.2 (2θ), 14.0±0.2 (2θ), 17.8±0.2 (2θ), 18.9±0.2 (2θ), and 21.0±0.2 (2θ).

Crystalline carvedilol dihydrogen phosphate methanol solvate (see, Example 3: Form II) is identified by an x-ray diffraction pattern as shown substantially in FIG. 24, which depicts characteristic peaks in degrees two-theta (2θ): i.e., 6.9±0.2 (2θ), 7.2±0.2 (2θ), 13.5±0.2 (2θ), 14.1±0.2 (2θ), 17.8±0.2 (2θ), and 34.0±0.2 (2θ).

Crystalline carvedilol dihydrogen phosphate dihydrate (see, Example 4: Form IV) is identified by an x-ray diffraction pattern as shown substantially in FIG. 25, which depicts characteristic peaks in degrees two-theta (2θ): i.e., 6.4±0.2 (2θ), 9.6±0.2 (2θ), 16.0±0.2 (2θ), 18.4±0.2 (2θ), 20.7±0.2 (2θ), and 24.5±0.2 (2θ).

Crystalline carvedilol dihydrogen phosphate (see, Example 5: Form V) is identified by an x-ray diffraction pattern as shown substantially in FIG. 28, which depicts characteristic peaks in degrees two-theta (2θ): i.e., 13.2±0.2 (2θ), 15.8±0.2 (2θ), 16.3±0.2 (2θ), 21.2±0.2 (2θ), 23.7±0.2 (2θ), and 26.0±0.2 (2θ).

Crystalline carvedilol hydrogen phosphate (see, Example 6: Form VI) is identified by an x-ray diffraction pattern as shown substantially in FIG. 29, which depicts characteristic peaks in degrees two-theta (2θ): i.e., 5.5±0.2 (2θ), 12.3±0.2 (2θ), 15.3±0.2 (2θ), 19.5±0.2 (2θ), 21.6±0.2 (2θ), and 24.6±0.2 (2θ).

The present invention also relates to a pharmaceutical composition, which contains a salt of carvedilol phosphate and/or corresponding solvates thereof.

Importantly, the chemical and/or physical properties of carvedilol forms described herein, which include salts of carvedilol dihydrogen phosphates, such as novel crystalline forms, and/or solvates thereof indicate that those forms may be particularly suitable for inclusion in medicinal agents, pharmaceutical compositions, etc.

For example, solubility of various carvedilol salts, and/or solvates as those described herein may facilitate provision or development of a dosage form from which the drug substance becomes available for bioabsorption throughout the gastrointestinal tract (i.e., in particular the lower small intestine and colon). In light of the foregoing, it may be possible to develop stable controlled release dosage forms containing such carvedilol phosphate salts and/or solvates of the present invention, etc., for once-per-day dosage, delayed release or pulsatile release to optimize therapy by matching pharmacokinetic performance with pharmacodynamic requirements.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art.

Thus, this invention also relates to a pharmaceutical composition comprising an effective amount of carvedilol dihydrogen phosphate salts and/or solvates thereof, with any of the characteristics noted herein, in association with one or more non-toxic pharmaceutically acceptable carriers and/or diluents thereof, and if desired, other active ingredients.

Moreover, the quantity of the compound or composition of the present invention administered will vary depending on the patient and the mode of administration and can be any effective amount.

Treatment regimen for the administration of the compounds and/or compositions of the present invention can also be determined readily by those with ordinary skill in art. The quantity of the compound and/or composition of the present invention administered may vary over a wide range to provide in a unit dosage an effective amount based upon the body weight of the patient per day to achieve the desired effect.

In particular, a composition of the present invention is presented as a unit dose and taken preferably from 1 to 2 times daily, most preferably once daily to achieve the desired effect.

Depending upon the treatment being effected, the compounds, and/or or compositions of the present invention can be administered orally, intravascularly, intraperitoneally, subcutaneously, intramuscularly or topically. Preferably, the composition is adapted for oral administration.

In general, pharmaceutical compositions of the present invention are prepared using conventional materials and techniques, such as mixing, blending and the like.

In accordance with the present invention, compounds and/or pharmaceutical composition can also include, but are not limited to, suitable adjuvants, carriers, excipients, or stabilizers, etc. and can be in solid or liquid form such as, tablets, capsules, powders, solutions, suspensions, or emulsions, etc.

Typically, the composition will contain a compound of the present invention, such as a salt of carvedilol or active compound(s), together with the adjuvants, carriers and/or excipients. In particular, a pharmaceutical composition of the present invention comprises an effective amount of a salt of carvedilol (i.e., such as carvedilol dihydrogen phosphate salts) and/or corresponding solvates (i.e., as identified herein) thereof, with any of the characteristics noted herein, in association with one or more non-toxic pharmaceutically acceptable carriers and/or diluents thereof, and if desired, other active ingredients.

In accordance with the present invention, solid unit dosage forms can be conventional types known in the art. The solid form can be a capsule and the like, such as an ordinary gelatin type containing the compounds of the present invention and a carrier, for example, lubricants and inert fillers such as, lactose, sucrose, or cornstarch, etc. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate, etc.

The tablets, capsules, and the like can also contain a binder, such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin, etc. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both, etc. A syrup can contain, in addition to active ingredient, sucrose as a sweetening agent, methyl and propylparabens as preservatives, a dye, and flavoring such as cherry or orange flavor, etc.

For oral therapeutic administration, these active compounds can be incorporated with excipients and used in the form of tablets, capsules, elixirs, suspensions, syrups, and the like. The percentage of the compound in compositions can, of course, be varied as the amount of active compound in such therapeutically useful compositions is such that a suitable dosage will be obtained.

Typically in accordance with the present invention, the oral maintenance dose is between about 25 mg and about 50 mg, preferably given once daily. In accordance with the present invention, the preferred unit dosage forms include tablets or capsules.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet, etc.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils, etc.

The compounds or pharmaceutical compositions of the present invention may also be administered in injectable dosages by solution or suspension of these materials in a physiologically acceptable diluent with a pharmaceutical adjuvant, carrier or excipients. Such adjuvants, carriers and/or excipients, include, but are not limited to sterile liquids, such as water and oils, with or without the addition of a surfactant and other pharmaceutically and physiologically acceptable carrier, including adjuvants, excipients or stabilizers, etc. Illustrative oils are those of petroleum, animal, vegetable, or synthetic origin, for example, peanut oil, soybean oil, or mineral oil, etc. In general, water, saline, aqueous dextrose and related sugar solution, and glycols, such as propylene glycol or polyethylene glycol, are preferred liquid carriers, particularly for injectable solutions, etc.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil, etc. In general, water, saline, aqueous dextrose and related sugar solution, and glycols such as, propylene glycol or polyethylene glycol, etc., are preferred liquid carriers, particularly for injectable solutions. Under ordinary conditions of storage and use, these preparations contain a preservative to prevent the growth of microorganisms.

The compounds and/or compositions prepared according to the present invention can be used to treat warm blooded animals, such as mammals, which include humans.

Conventional administration methods may be suitable for use in the present invention.

The present invention further relates to a method of treating hypertension, congestive heart failure and angina, which comprises administering to a subject in need thereof an effective amount of a carvedilol phosphate salt (i.e., which include novel crystalline forms) and/or solvates thereof or a pharmaceutical composition (i.e., which contains such salts and/or solvates of carvedilol phosphate), etc.

The Examples set forth below are illustrative of the present invention and are not intended to limit, in any way, the scope of the present invention.

EXAMPLES

Example 1

Form I Carvedilol Dihydrogen Phosphate Hemihydrate Preparation

A suitable reactor is charged with acetone. The acetone solution is sequentially charged with carvedilol and water. Upon addition of the water, the slurry dissolves quicky. To the solution is added aqueous $H_3PO_4$. The reaction mixture is stirred at room temperature and carvedilol dihydrogen phosphate seeds are added in one portion. The solid precipitate formed is stirred, then filtered and the collected cake is washed with aqueous acetone. The cake is dried under vacuum to a constant weight. The cake is weighed and stored in a polyethylene container.

Example 2

Form II Carvedilol Dihydrogen Phosphate Dihydrate Preparation

Form I is slurried in acetone/water mixture between 10 and 30° C. for several days.

Example 3

Form III Carvedilol Dihydrogen phosphate Methanol Solvate Preparation

Form I is slurried in methanol between 10 and 30° C. for several days.

Example 4

Form IV—Carvedilol Dihydrogen Phosphate Dihydrate Preparation

Carvedilol dihydrogen dihydrogen phosphate is dissolved in an acetone/water mixture. The acetone is removed by distillation. A solid crystallizes during acetone removal and is filtered and dried.

Example 5

Form V—Carvedilol Dihydrogen Phosphate Preparation

Carvedilol dihydrogen phosphate hemihydrate (Form I) was suspended in water, and the suspension was placed on a mechanical shaker at room temperature. After 48 hours of shaking, the solid was isolated from suspension by filtration, then dried in a desiccator under vacuum for a few days.

Example 6

Form VI—Carvedilol Hydrogen Phosphate Preparation

A suitable reactor is charged with acetone. The acetone solution is sequentially charged with SK&F 105517 and water. Upon addition of the water, the slurry dissolves quicky. To the solution is added aqueous $H_3PO_4$ (at ½ the molar quantity of Carvedilol). The reaction mixture is stirred and allowed to crystallize. The solid precipitate formed is stirred and cooled, then filtered and the collected cake is washed with aqueous acetone.

Example 7

$^{13}C$ and $^{31}P$ Solid State NMR Data Analysis of Carvedilol Dihydrogen Phosphate Hemihydrate (Form I)

A sample of carvedilol dihydrogen phosphate hemihydrate (Form I) was analyzed by solid-state $^{13}C$ NMR and $^{31}P$ NMR (i.e., to probe solid compound form structure).

Carvedilol dihydrogen phosphate (Parent MW=406.5; Salt MW=504.5) has the following structure and numbering scheme:

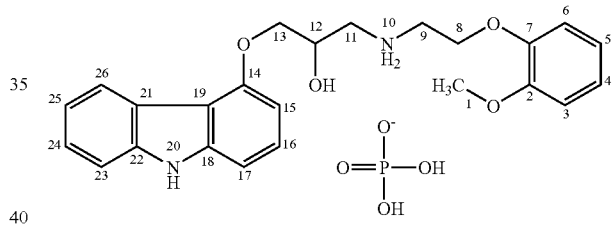

Experimental Details and $^{13}C$ and $^{31}P$ Analysis

The solid state $^{13}C$ NMR methods used to analyze compounds of the present invention produce a qualitative picture of the types of carbon sites within the solid material. Because of variable polarization transfer rates and the need for sideband suppression, the peak intensities are not quantitative (much like the case in solution-state $^{13}C$ NMR). However, the $^{31}P$ spectra are inherently quantitative.

For the $^{13}C$ analysis, approximately 100 mg of sample was packed into a 7-mm O.D. magic-angle spinning rotor and spun at 5 kHz. The $^{13}C$ spectrum of the sample was recorded using a CP-TOSS pulse sequence (cross-polarization with total suppression of sidebands). An edited spectrum containing only quaternary and methyl carbons was then obtained using an CP-TOSS sequence with NQS (non-quaternary suppression). The $^{13}C$ spectra are referenced externally to tetramethylsilane via a sample of solid hexamethylbenzene.

For $^{31}P$ Solid State NMR, approximately 40 mg of sample was packed into a 4-mm O.D. rotor and spun at 10 kHz. Both CP-MAS and single-pulse MAS $^{31}P$ pulse sequences were used with $^1H$ decoupling. The $^{31}P$ data are externally referenced to 85% phosphoric acid by a secondary solid-state reference (triphenylphosphine oxide). The Bruker AMX2-360 spectrometer used for this work operates at $^{13}C$, $^{31}P$ and $^1$H frequencies of 90.556, 145.782 and 360.097 MHz, respectively. All spectra were obtained at 298 K.

Results and Discussion

The highly sensitive $^{13}$C and $^{31}$P Solid State NMR identification methods were used for the analysis and characterization of a polymorphic form of Carvedilol phosphate, which confirms its chemical structure in the solid-state.

The form of Carvedilol dihydrogen phosphate is defined by these spectra, where both $^{13}$C and $^{31}$P spectra show clear and distinct differences.

Figure 26:
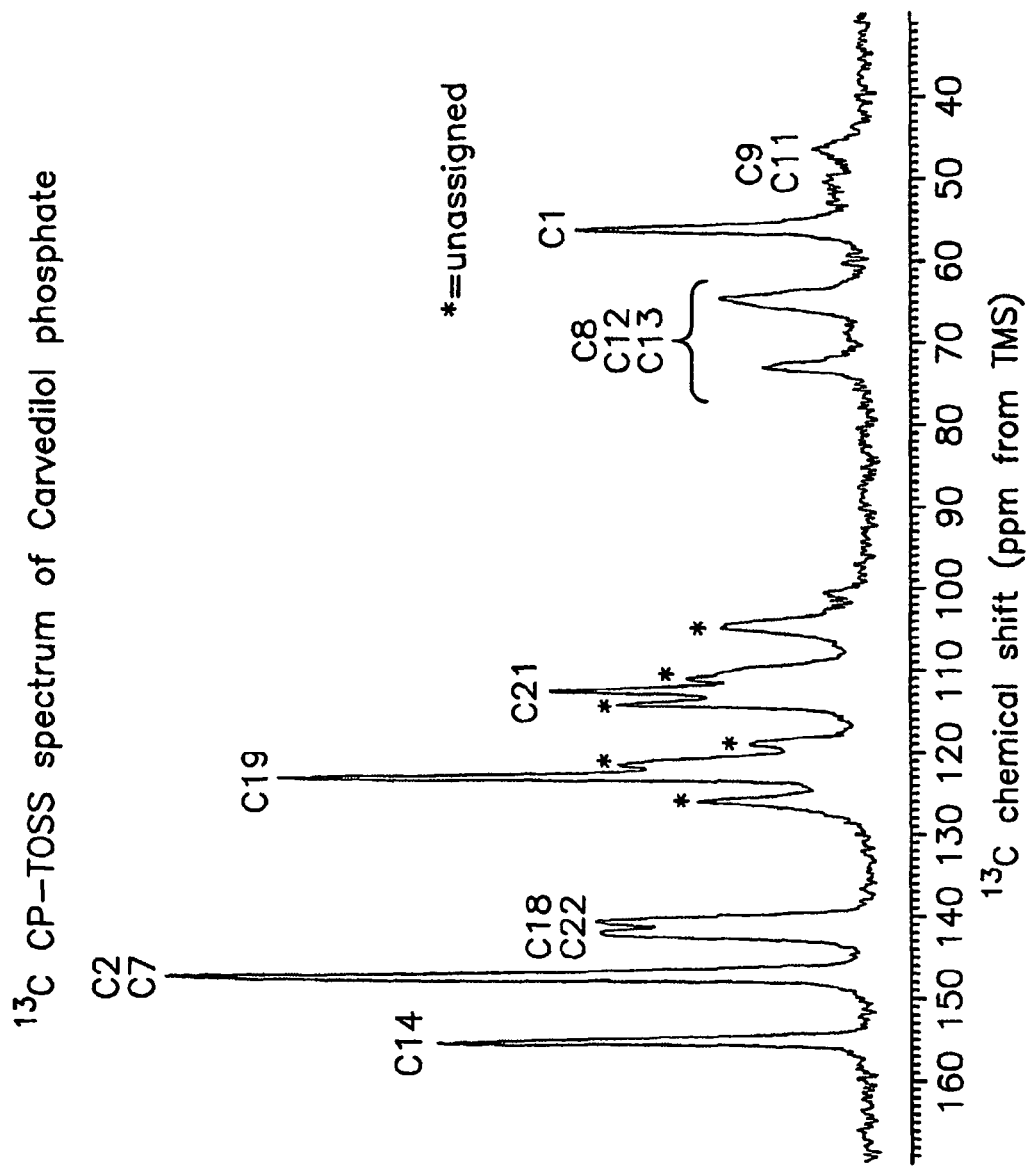
FIG. 26 is a solid state $^{13}C$ NMR for carvedilol dihydrogen phosphate dihydrate (Form I).

In particular, FIG. 26 shows the $^{13}$C CP-TOSS spectrum of carevedilol dihydrogen phosphate. An assignment of the numerous $^{13}$C resonances in FIG. 1 can be made by chemical shift assignment, the NQS spectrum and comparisons with solution-state $^{13}$C assignments. At least two non-equivalent molecules per unit cell are observed in this form of Carvedilol phosphate.

Figure 27:
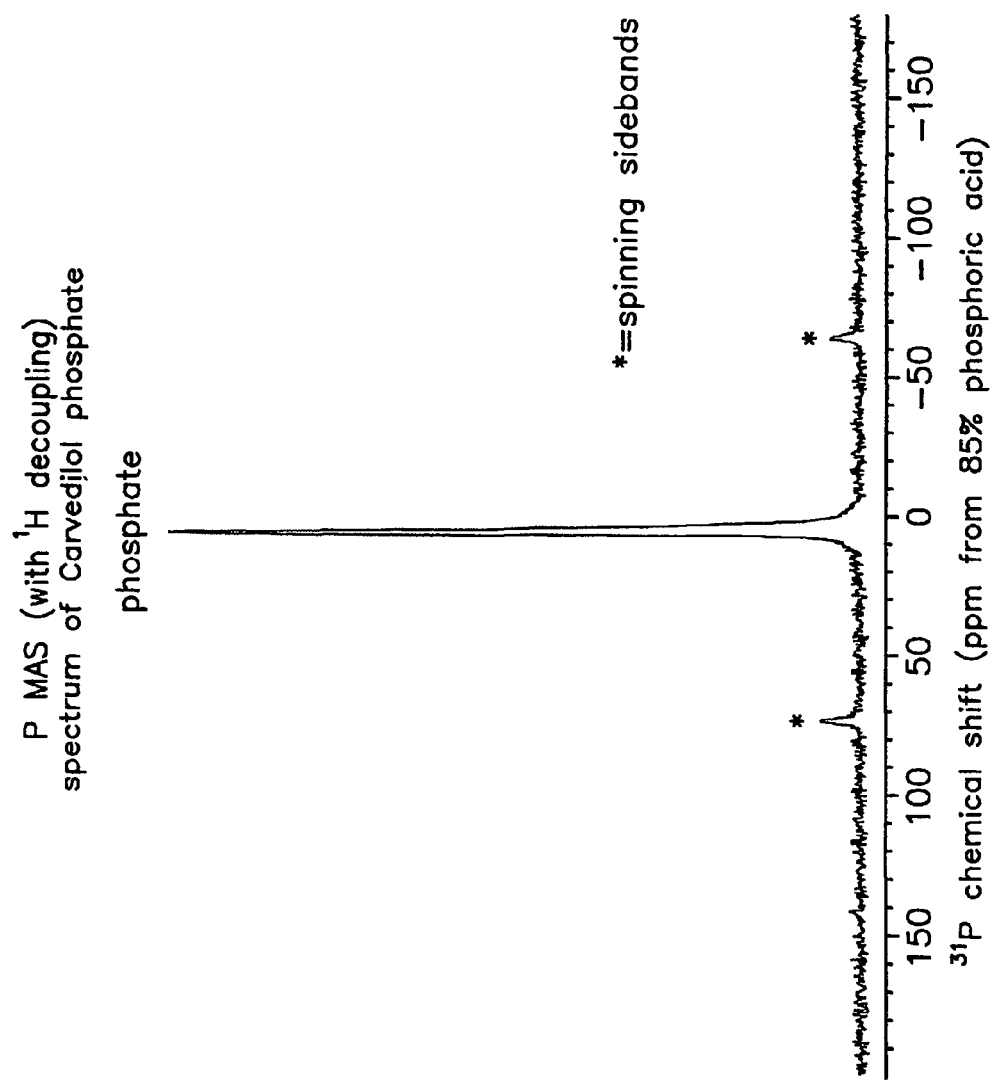
FIG. 27 is a solid state $^{31}P$ NMR for carvedilol dihydrogen phosphate dihydrate (Form I).
Figure 28:
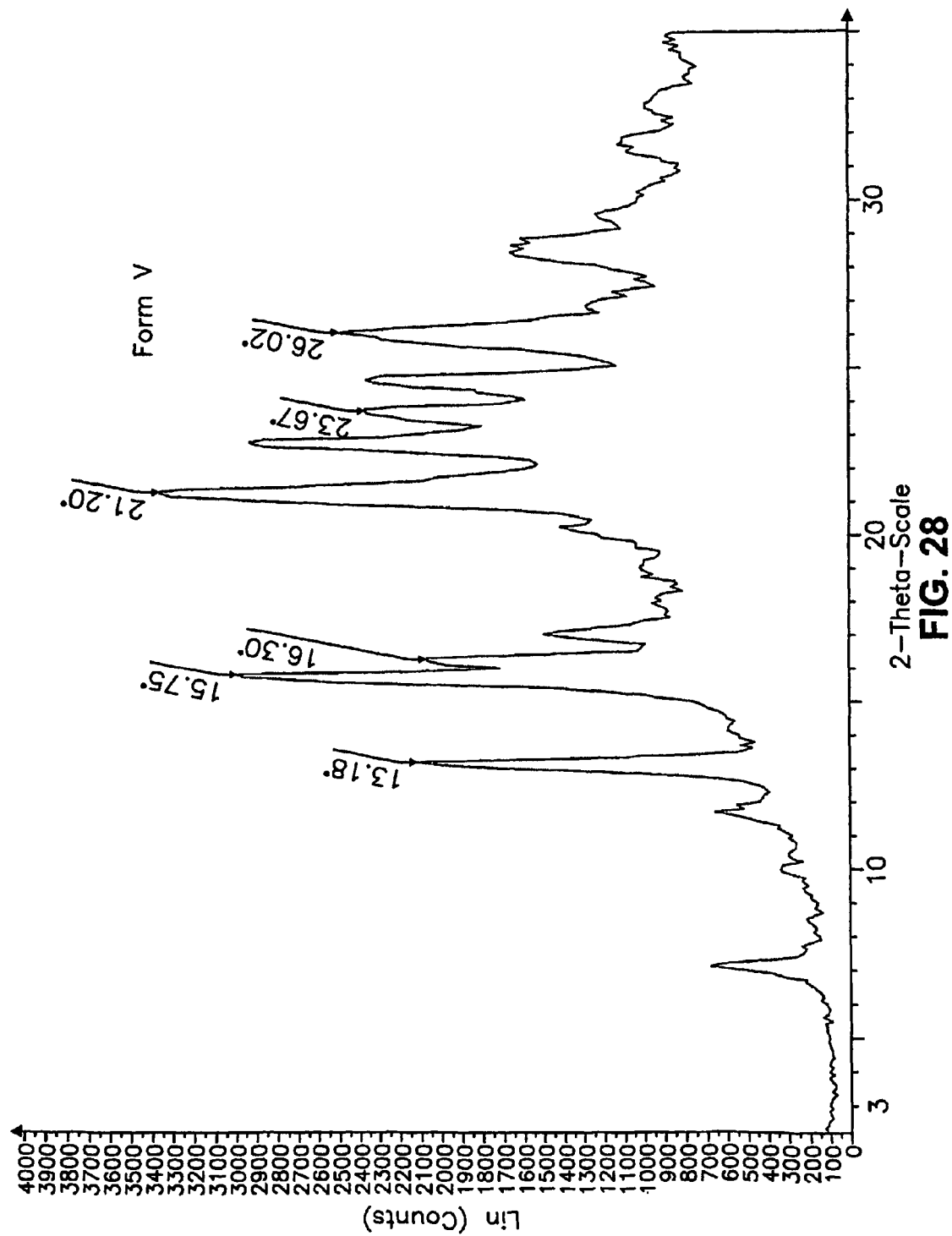
FIG. 28 is an x-ray powder diffractogram for carvedilol dihydrogen phosphate (Form V).
Figure 29:
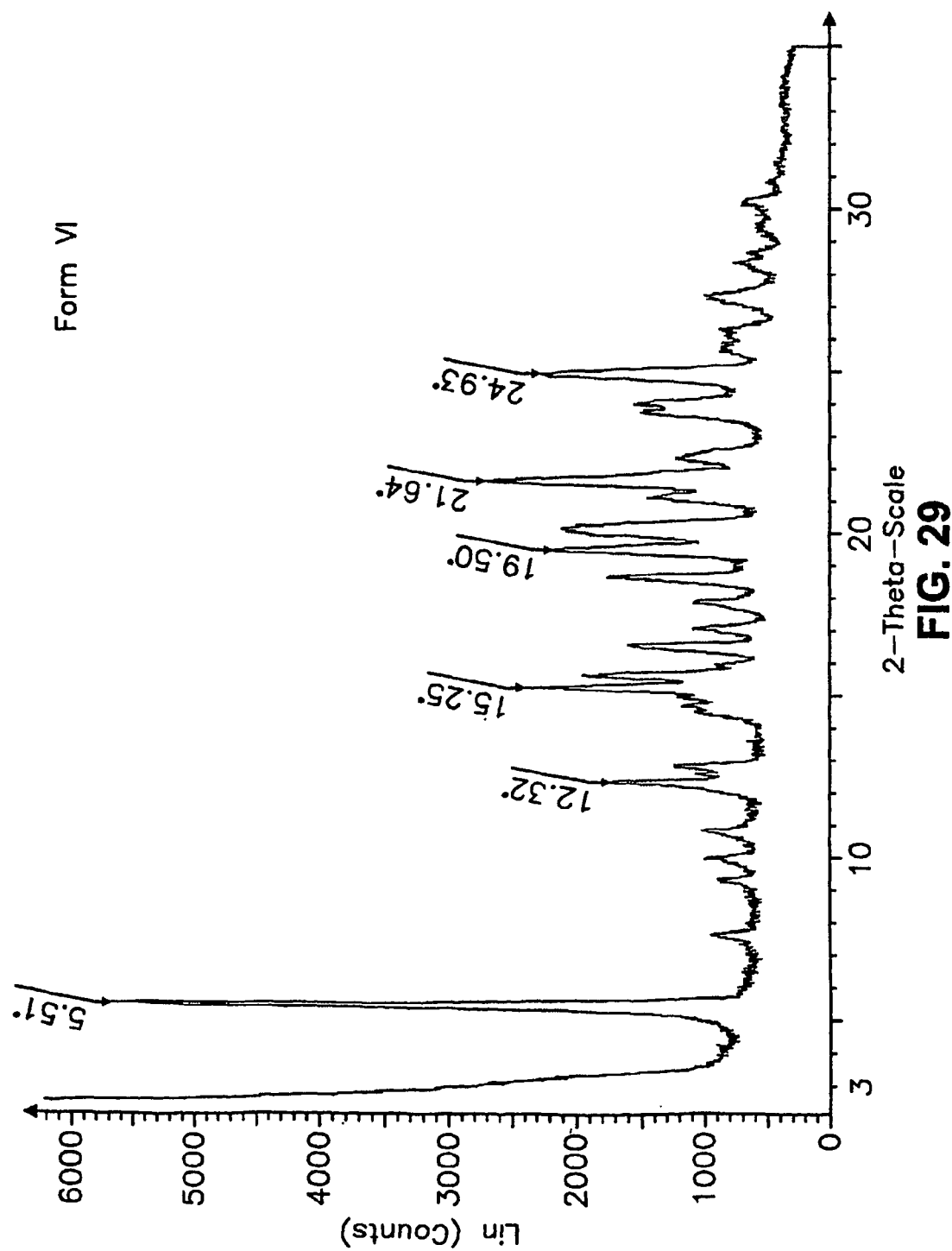
FIG. 29 is an x-ray powder diffractogram for carvedilol hydrogen phosphate (Form VI).

FIG. 27 shows the $^{31}$P MAS spectrum of carvedilol dihydrogen phosphate. A single phosphorus signal is observed at 4.7 ppm, which is characteristic of phosphate salts.

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is crystalline carvedilol dihydrogen phosphate hemihydrate.

Figure 1:
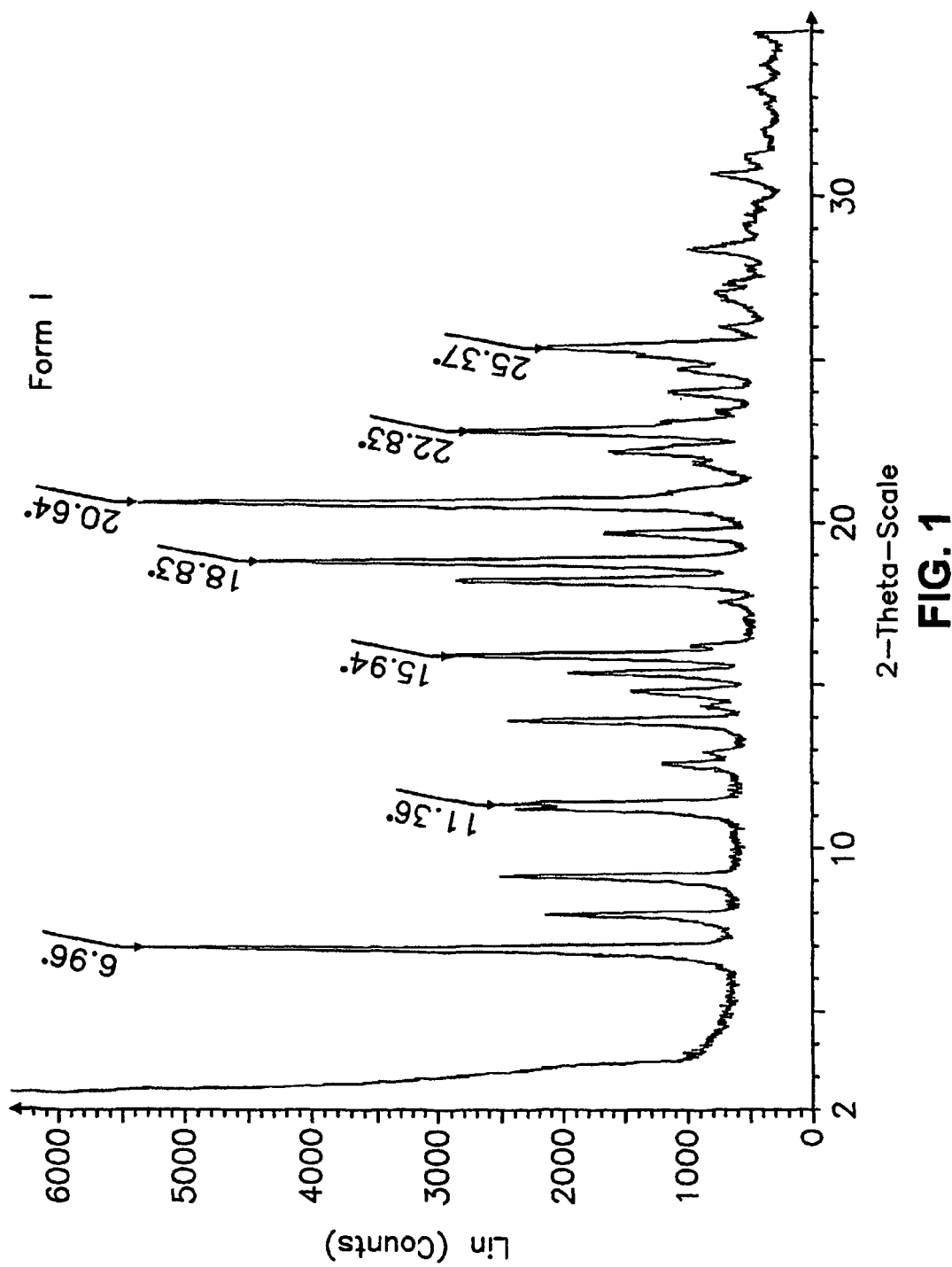
FIG. 1 is an x-ray powder diffractogram for carvedilol dihydrogen phosphate hemihydrate (Form I).
Figure 2:
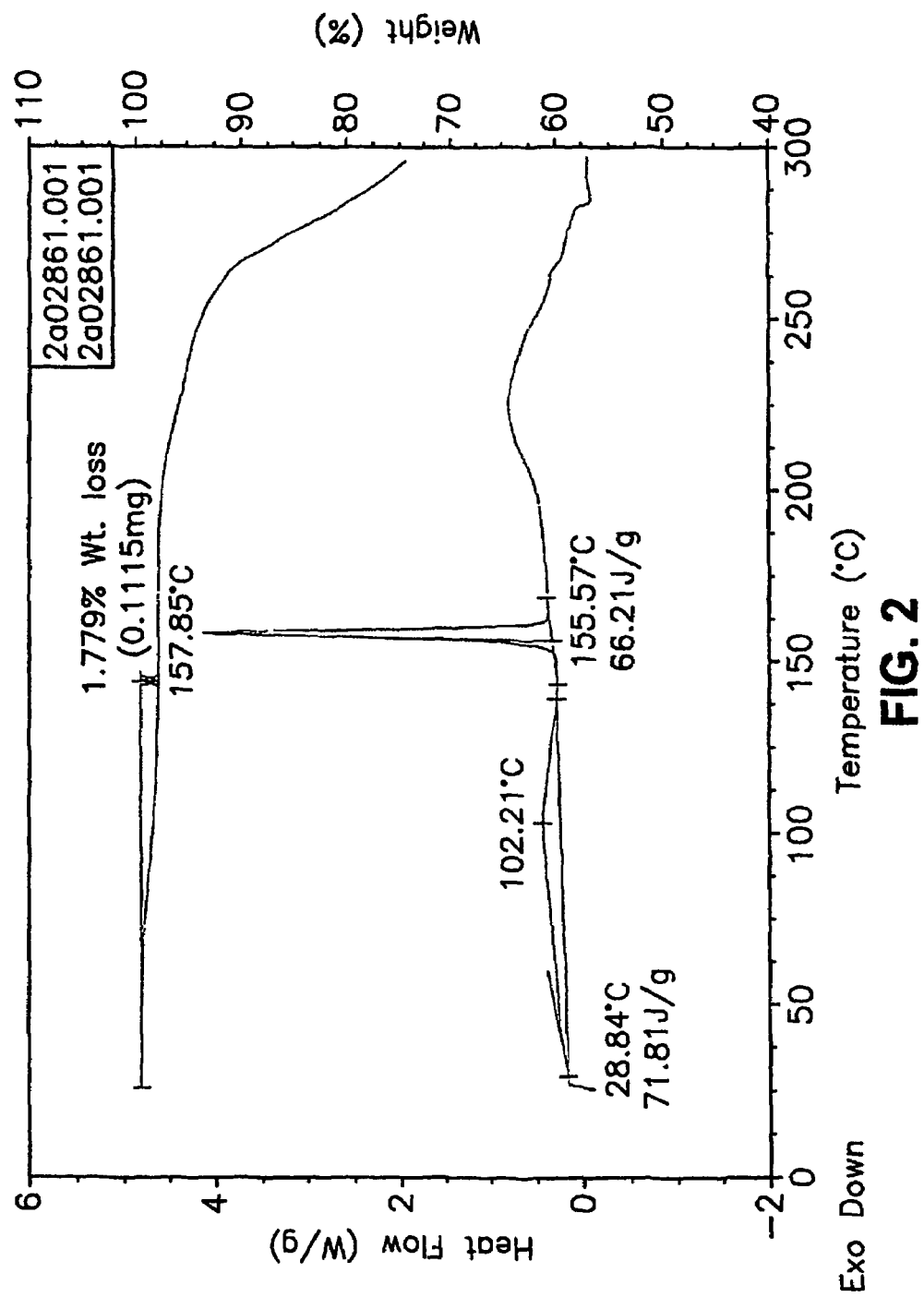
FIG. 2 shows the thermal analysis results for carvedilol dihydrogen phosphate hemihydrate (Form I).

2. The compound according to claim 1 having an x-ray diffraction pattern which comprises characteristic peaks in degrees two-theta as shown in FIG. 1.

3. The compound according to claim 2 having characteristic peaks from 0° degrees 2-theta (2θ) to 35° degrees 2-theta (2θ) at about 7.0±0.2 (2θ), 11.4±0.2 (2θ), 15.9±0.2 (2θ), 18.8±0.2 (2θ), 20.6±0.2 (2θ), 22.8±0.2 (2θ), and 25.4±0.2 (2θ).

Figure 6:
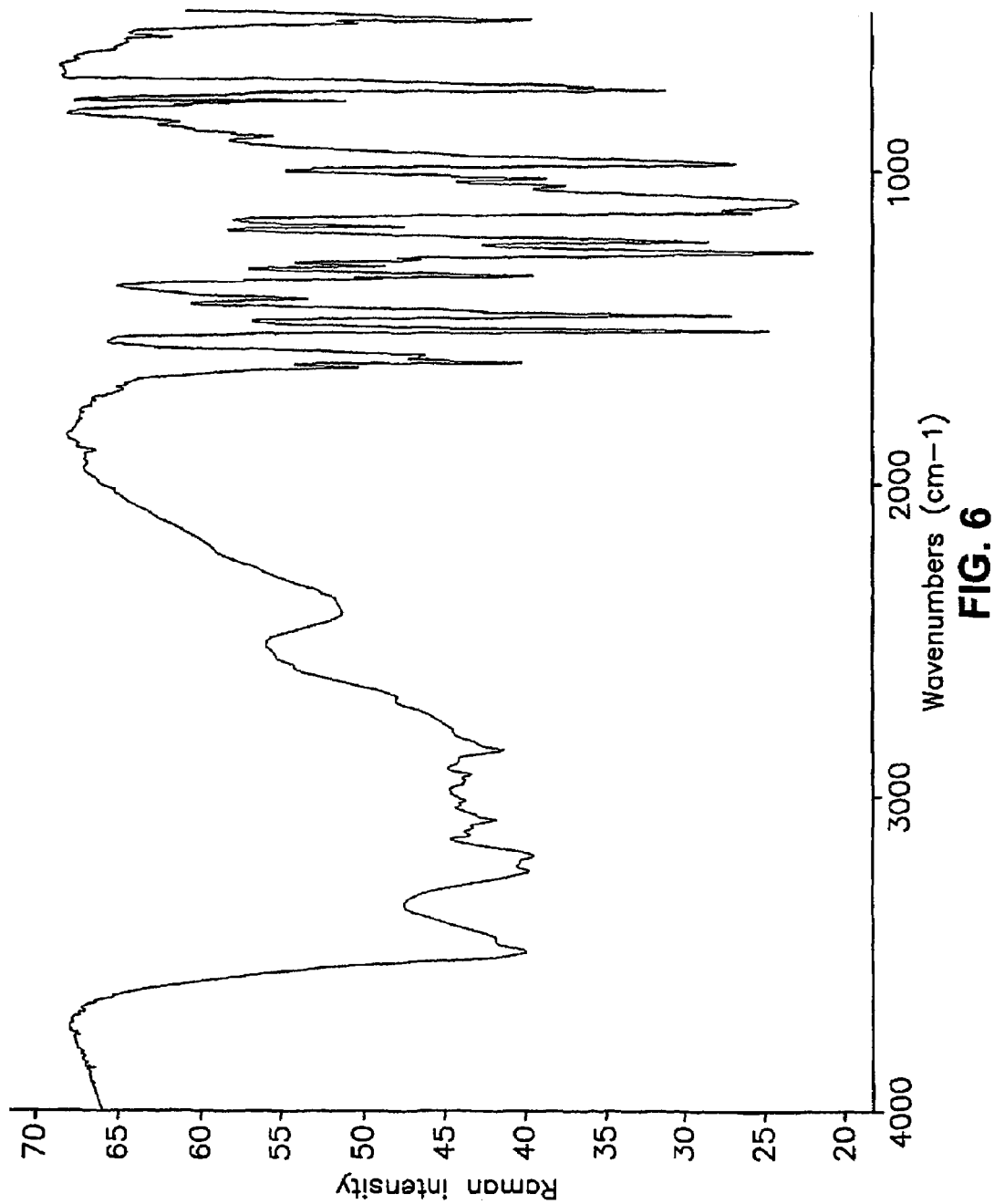
FIG. 6 is an FT-IR spectrum for carvedilol dihydrogen phosphate hemihydrate (Form I).
Figure 7:
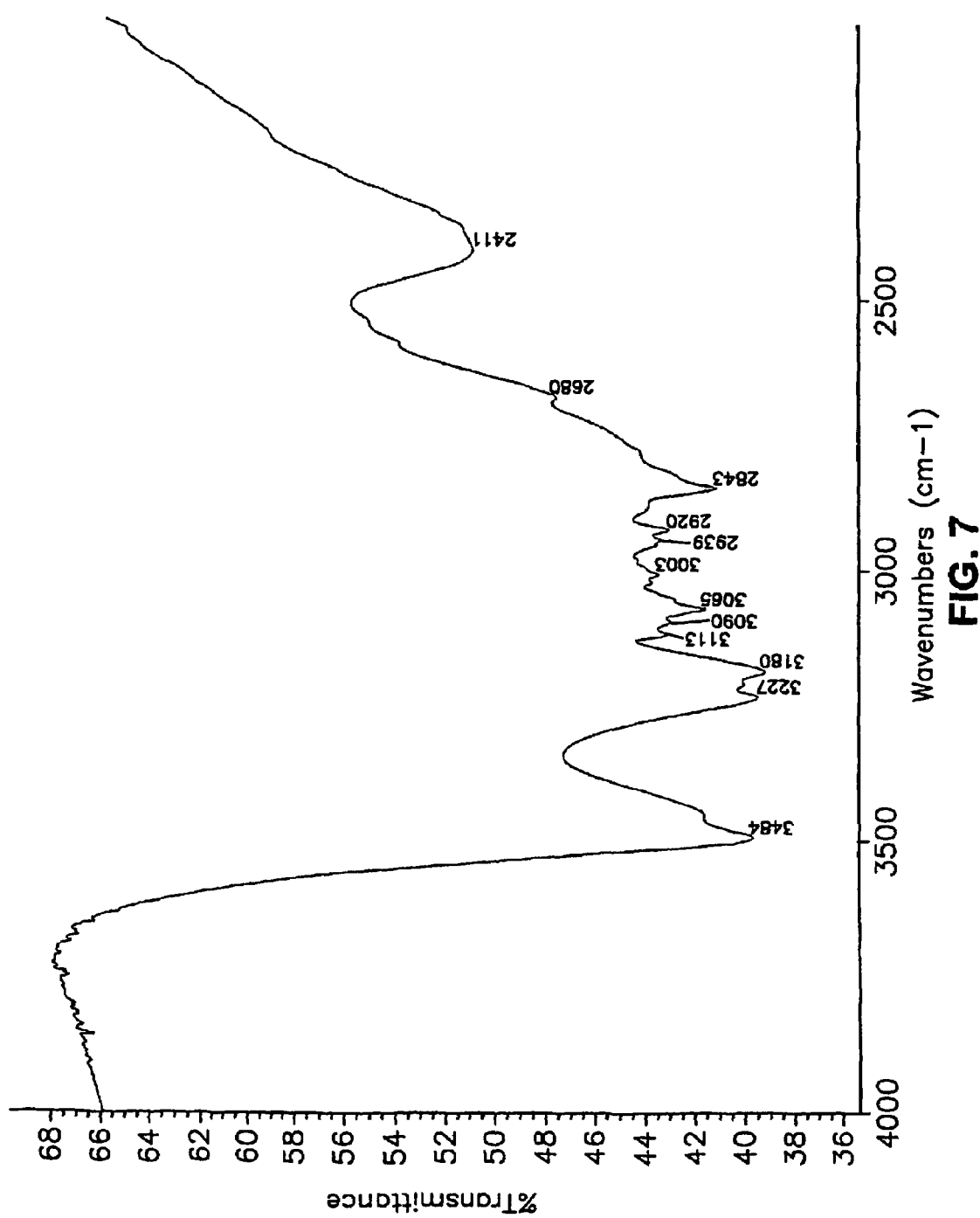
FIG. 7 is an FT-IR spectrum for carvedilol dihydrogen phosphate hemihydrate in the 4000-2000 $cm^{-1}$ region of the spectrum (Form I).
Figure 8:
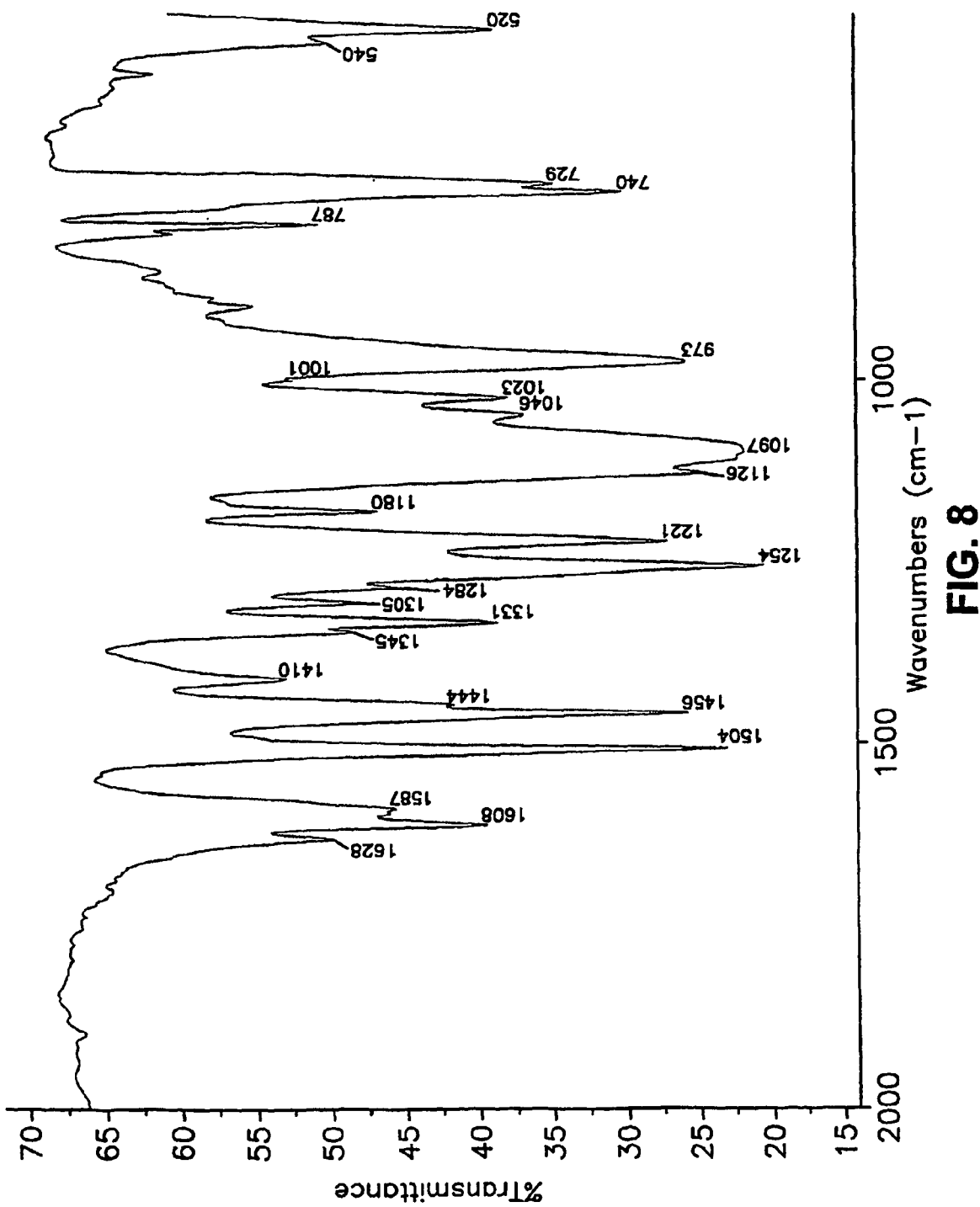
FIG. 8 is an FT-IR spectrum for carvedilol dihydrogen phosphate hemihydrate in the 2000-500 $cm^{-1}$ region of the spectrum (Form I).

4. The compound according to claim 1 having an infrared spectrum which comprises characteristic absorption bands expressed in wave numbers as shown in FIG. 6.

Figure 3:
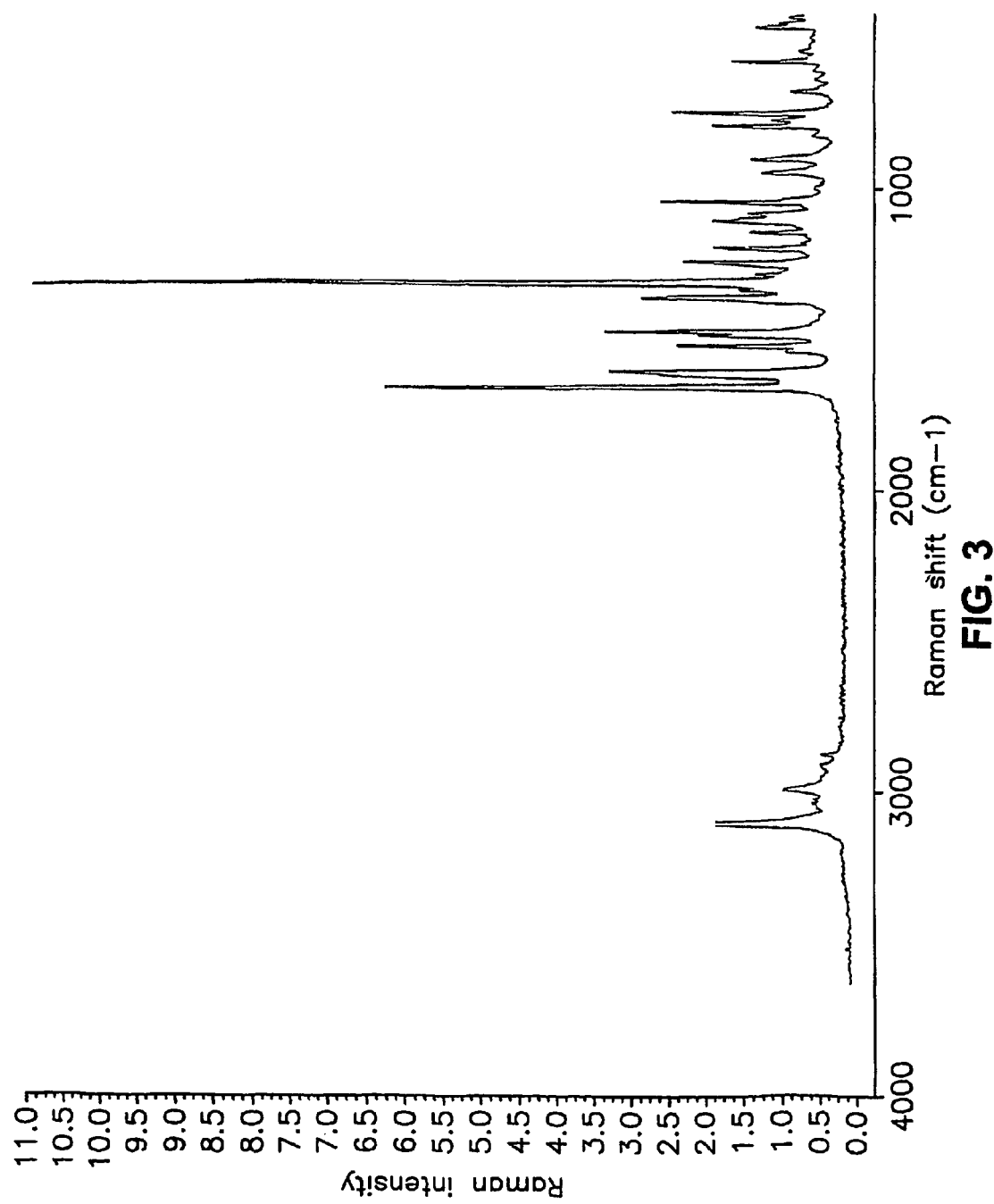
FIG. 3 is an FT-Raman spectrum for carvedilol dihydrogen phosphate hemihydrate (Form I).
Figure 4:
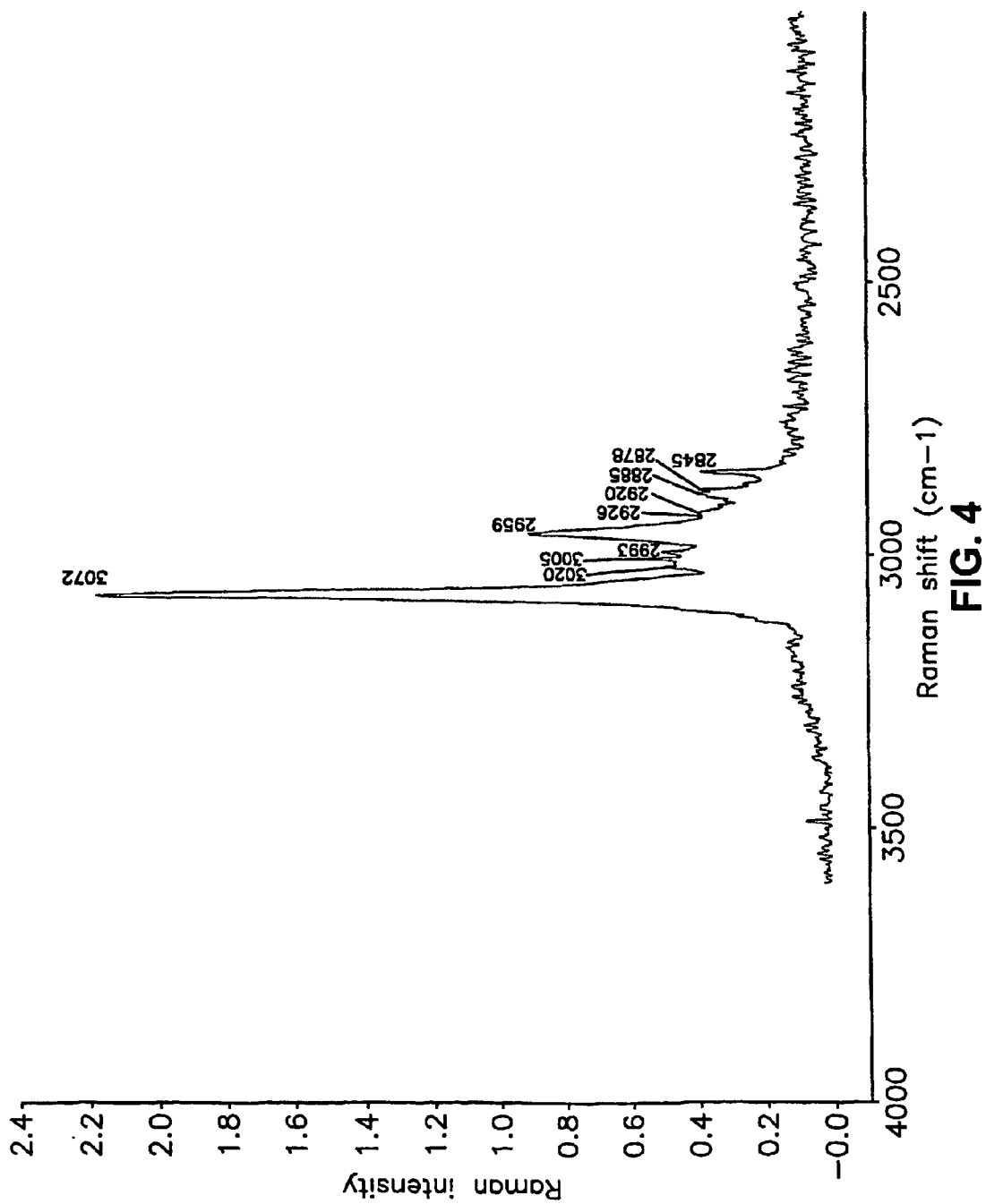
FIG. 4 is an FT-Raman spectrum for carvedilol dihydrogen phosphate hemihydrate in the 4000-2000 $cm^{-1}$ region of the spectrum (Form I).
Figure 5:
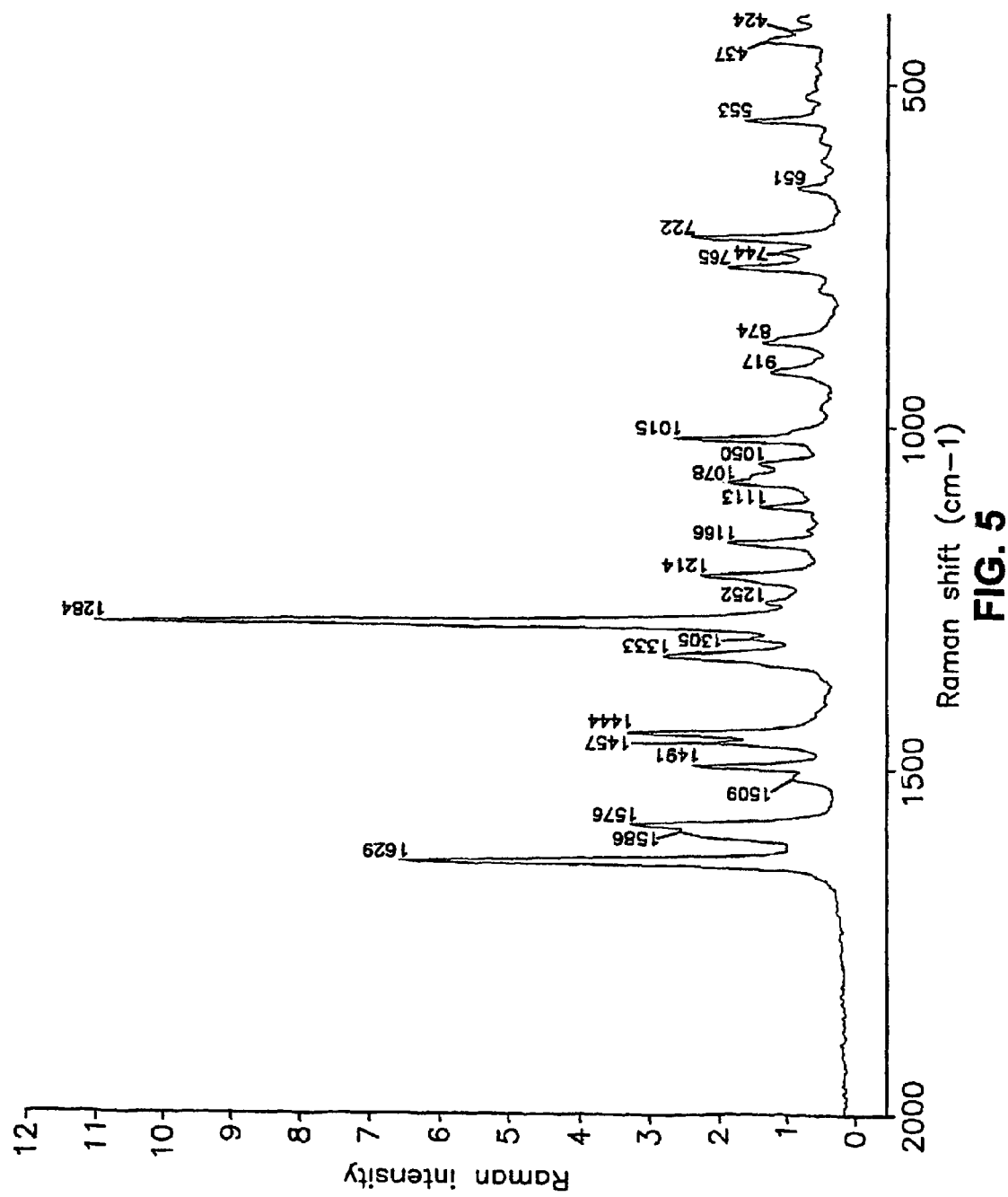
FIG. 5 is an FT-Raman spectrum for carvedilol dihydrogen phosphate hemihydrate in the 2000-400 $cm^{-1}$ region of the spectrum (Form I).

5. The compound according to claim 1 having a Raman spectrum which comprises characteristic peaks as shown in FIG. 3.

6. A pharmaceutical composition comprising the compound according to claim 1 and a pharmaceutically acceptable carrier.

7. A method of treating hypertension, congestive heart failure or angina which comprises administering to a subject in need thereof an effective amount of the compound according to claim 1.

8. A method of treating hypertension, congestive heart failure or angina which comprises administering to a subject in need thereof an effective amount of the composition according to claim 6.

* * * * *